United States Patent
Sigurjonsson et al.

(10) Patent No.: US 7,459,598 B2
(45) Date of Patent: Dec. 2, 2008

(54) WOUND DRESSING

(75) Inventors: Gudmundur Fertram Sigurjonsson, Reykjavik (IS); Thordur M. Elefsen, Mosfellsbaer (IS)

(73) Assignee: Ossur, hf, Reykjavik (IS)

( * ) Notice: Subject to any disclaimer, the term of this patent is extended or adjusted under 35 U.S.C. 154(b) by 688 days.

(21) Appl. No.: 10/725,632

(22) Filed: Dec. 3, 2003

(65) Prior Publication Data

US 2004/0127836 A1 Jul. 1, 2004

Related U.S. Application Data

(60) Provisional application No. 60/518,317, filed on Nov. 10, 2003, provisional application No. 60/503,546, filed on Sep. 17, 2003, provisional application No. 60/482,775, filed on Jun. 27, 2003, provisional application No. 60/437,146, filed on Dec. 31, 2002.

(51) Int. Cl.
*A61F 13/00* (2006.01)
(52) U.S. Cl. ............... 602/48; 602/41; 602/42
(58) Field of Classification Search ......... 424/444–449; 602/41–59; 128/888, 889; D24/189; 206/440, 206/441; 604/304–308
See application file for complete search history.

(56) References Cited

U.S. PATENT DOCUMENTS

| | | | |
|---|---|---|---|
| 2,649,088 A | 8/1953 | Sigg | |
| 2,764,976 A | 10/1956 | Skiles | |
| 3,006,338 A | 10/1961 | Davies | |
| 3,042,549 A | 7/1962 | Arnold | |
| 3,113,568 A | 12/1963 | Robins | |
| 3,156,242 A | 11/1964 | Crowe, Jr. | |
| 3,292,619 A | 12/1966 | Egler | |
| 3,307,545 A | 3/1967 | Surowitz | |
| 3,645,835 A | 2/1972 | Hodgson | |
| 3,678,933 A | 7/1972 | Moore et al. | |
| 3,814,101 A | 6/1974 | Kozak | |
| 3,927,669 A | 12/1975 | Glatt | |
| 3,972,328 A | 8/1976 | Chen | |
| 4,034,751 A | 7/1977 | Hung | |
| 4,055,180 A | 10/1977 | Karami | |
| 4,175,557 A | 11/1979 | Hung | |
| 4,212,296 A | 7/1980 | Schaar | |
| 4,360,021 A | 11/1982 | Stima | |
| 4,373,519 A | 2/1983 | Errede et al. | |

(Continued)

FOREIGN PATENT DOCUMENTS

CA 724612 12/1965

(Continued)

OTHER PUBLICATIONS

Perkins, K., et al., "Silicone gel: a new treatment for burn scars and contractures", Burns, vol. 9, No. 1.

(Continued)

*Primary Examiner*—Kim M Lewis
(74) *Attorney, Agent, or Firm*—Bacon & Thomas, PLLC

(57) ABSTRACT

A wound dressing including at least one skin adherent facing layer comprising a discrete layer of silicone gel having a plurality of preformed apertures arranged in a pattern. The pattern of apertures may be equally spaced and generally uniform in shape. The wound dressing may include a facing layer with at least two discrete, adjacent silicone gel layers having different strength properties.

12 Claims, 10 Drawing Sheets

U.S. PATENT DOCUMENTS

| | | |
|---|---|---|
| 4,408,996 A | 10/1983 | Baldwin |
| 4,538,603 A | 9/1985 | Pawelchak et al. |
| 4,560,372 A | 12/1985 | Pieniak |
| 4,603,076 A | 7/1986 | Bowditch et al. |
| 4,614,183 A | 9/1986 | McCracken et al. |
| 4,635,624 A | 1/1987 | Gilman |
| 4,655,210 A | 4/1987 | Edenbaum et al. |
| 4,657,006 A | 4/1987 | Rawlings et al. |
| 4,661,099 A | 4/1987 | von Bittera |
| 4,664,106 A | 5/1987 | Snedeker |
| 4,684,557 A | 8/1987 | Pennace |
| 4,690,683 A | 9/1987 | Chien |
| 4,699,146 A | 10/1987 | Sieverding |
| 4,733,659 A | 3/1988 | Edenbaum et al. |
| 4,738,257 A | 4/1988 | Meyer et al. |
| 4,750,482 A | 6/1988 | Sieverding |
| 4,753,231 A | 6/1988 | Lang et al. |
| 4,762,680 A | 8/1988 | Pennace |
| 4,773,408 A | 9/1988 | Cilento |
| 4,838,253 A | 6/1989 | Brassington et al. |
| 4,846,164 A | 7/1989 | Martz |
| 4,860,737 A | 8/1989 | Lang et al. |
| 4,867,748 A | 9/1989 | Samuelsen |
| 4,906,240 A | 3/1990 | Reed et al. |
| 4,921,704 A | 5/1990 | Fabo |
| 4,950,148 A | 8/1990 | Nakanishi |
| 4,977,892 A | 12/1990 | Ewall |
| 4,985,277 A | 1/1991 | Shimizu et al. |
| 4,991,574 A | 2/1991 | Pocknell |
| 4,995,382 A | 2/1991 | Lang et al. |
| 5,010,883 A | 4/1991 | Rawlings et al. |
| 5,074,944 A | 12/1991 | Trenka |
| 5,088,483 A | 2/1992 | Heinecke |
| 5,147,338 A | 9/1992 | Lang et al. |
| 5,160,328 A | 11/1992 | Cartmell et al. |
| 5,167,613 A | 12/1992 | Karami et al. |
| 5,244,457 A | 9/1993 | Karami et al. |
| 5,279,890 A | 1/1994 | Ikeno |
| 5,322,729 A | 6/1994 | Heeter |
| 5,340,363 A | 8/1994 | Fabo |
| 5,352,508 A | 10/1994 | Cheong |
| 5,362,508 A | 11/1994 | Wheeler |
| 5,395,305 A | 3/1995 | Koide et al. |
| 5,409,472 A | 4/1995 | Rawlings et al. |
| 5,445,604 A | 8/1995 | Lang |
| 5,486,158 A | 1/1996 | Samuelsen |
| 5,489,262 A | 2/1996 | Cartmell et al. |
| 5,512,041 A | 4/1996 | Bogart |
| 5,540,922 A | 7/1996 | Fabo |
| 5,556,375 A | 9/1996 | Ewall |
| 5,571,529 A | 11/1996 | Cheong |
| 5,591,820 A | 1/1997 | Kydonieus et al. |
| 5,593,395 A | 1/1997 | Martz |
| 5,603,946 A | 2/1997 | Constantine |
| 5,607,388 A | 3/1997 | Ewall |
| 5,629,014 A | 5/1997 | Kwiatek et al. |
| 5,633,007 A | 5/1997 | Webb et al. |
| 5,635,201 A | 6/1997 | Fabo |
| 5,653,699 A | 8/1997 | Reed et al. |
| 5,681,579 A | 10/1997 | Freeman |
| 5,738,642 A | 4/1998 | Heinecke |
| 5,759,560 A | 6/1998 | Dillon |
| 5,782,787 A | 7/1998 | Webster |
| 5,847,003 A * | 12/1998 | Ptchelintsev et al. ........ 514/532 |
| 5,891,076 A | 4/1999 | Fabo |
| 5,914,125 A | 6/1999 | Andrews et al. |
| 5,919,476 A | 7/1999 | Fischer |
| 5,925,439 A | 7/1999 | Haubach |
| 5,941,840 A | 8/1999 | Court et al. |
| 5,942,332 A | 8/1999 | Nakamura |
| 5,973,221 A | 10/1999 | Collyer et al. |
| 5,981,822 A | 11/1999 | Addison |
| 6,040,492 A | 3/2000 | Lindquist et al. |
| 6,051,317 A | 4/2000 | Brueggemann et al. |
| 6,051,747 A | 4/2000 | Lindqvist et al. |
| 6,066,773 A | 5/2000 | Freeman |
| 6,103,369 A | 8/2000 | Lucast et al. |
| 6,107,536 A | 8/2000 | Dadinis |
| 6,136,039 A * | 10/2000 | Kristinsson et al. ........... 623/36 |
| 6,149,614 A | 11/2000 | Dunshee et al. |
| 6,200,195 B1 | 3/2001 | Furuno |
| 6,207,875 B1 * | 3/2001 | Lindqvist et al. .............. 602/46 |
| 6,242,665 B1 | 6/2001 | Malowaniec |
| 6,291,050 B1 | 9/2001 | Cree |
| 6,320,093 B1 | 11/2001 | Augustine et al. |
| 6,333,093 B1 | 12/2001 | Burrell |
| 6,420,622 B1 | 7/2002 | Johnston |
| 6,461,467 B2 * | 10/2002 | Blatchford et al. .......... 156/230 |
| 6,472,581 B1 | 10/2002 | Muramatsu |
| 6,479,724 B1 | 11/2002 | Areskoug et al. |
| 6,485,776 B2 * | 11/2002 | Janusson et al. ........... 427/2.31 |
| 6,552,244 B1 | 4/2003 | Jacques et al. |
| 6,559,351 B1 | 5/2003 | Eakin |
| 6,566,575 B1 | 5/2003 | Stickels et al. |
| 6,566,576 B1 | 5/2003 | Komerska et al. |
| 6,566,577 B1 | 5/2003 | Addison et al. |
| 6,600,085 B2 | 7/2003 | Sun et al. |
| 6,610,411 B2 | 8/2003 | Daoud et al. |
| 6,649,804 B2 | 11/2003 | Eakin |
| 6,653,520 B1 | 11/2003 | Mouton |
| 7,119,247 B2 | 10/2006 | Worthley |
| 2002/0156410 A1 | 10/2002 | Lawry |
| 2002/0193723 A1 | 12/2002 | Batdorf, Sr. et al. |
| 2003/0040691 A1 | 2/2003 | Griesbach, III et al. |
| 2003/0059626 A1 | 3/2003 | Daoud |
| 2003/0088202 A1 | 5/2003 | Gilman |
| 2003/0120229 A1 | 6/2003 | de Jong et al. |
| 2003/0125654 A1 | 7/2003 | Malik |
| 2003/0167028 A1 | 9/2003 | Binder et al. |
| 2003/0194526 A1 | 10/2003 | Vesley et al. |
| 2003/0199800 A1 | 10/2003 | Levin |
| 2003/0204159 A1 | 10/2003 | Lawry |
| 2006/0129081 A1 * | 6/2006 | Binder et al. ................. 602/60 |

FOREIGN PATENT DOCUMENTS

| | | |
|---|---|---|
| EP | 0106440 | 11/1987 |
| EP | 0413251 | 11/1994 |
| EP | 0 799 693 A2 | 10/1997 |
| EP | 1374813 A2 | 1/2004 |
| GB | 778813 | 7/1957 |
| GB | 898826 | 6/1962 |
| GB | 1280631 | 7/1972 |
| GB | 1398011 | 6/1975 |
| GB | 2061732 | 5/1981 |
| GB | 2074029 | 10/1981 |
| GB | 2093702 | 9/1982 |
| GB | 2093703 | 9/1982 |
| JP | 05069512 A | 3/1993 |
| WO | WO89/08555 | 9/1989 |
| WO | WO02062403 A1 | 8/2002 |
| WO | WO03026544 A1 | 4/2003 |
| WO | WO03043553 A1 | 5/2003 |
| WO | WO03045294 A1 | 6/2003 |
| WO | WO03055536 A1 | 7/2003 |
| WO | WO03057103 A1 | 7/2003 |
| WO | WO03061538 A1 | 7/2003 |
| WO | WO03061539 A1 | 7/2003 |
| WO | WO03068283 A2 | 8/2003 |
| WO | WO03086255 A1 | 10/2003 |

OTHER PUBLICATIONS

Smith & Nephew—Cutinova* Hydro downloaded on Apr. 29, 2004 at http://wound.smith-nephew.com/us/Standard.asp?NodeId=2608.

Krieser, Jason, K., et al., "Comparison of Hydrophilic Polyurethane Foam Dressings", downloaded on Jun. 16, 2003, at http://woundcare.org/newsvol2n2/pr12.htm.

Moist Wound Healing, downloaded Jun. 16, 2003 at http://www.lawrenceville.org/_mgolden/moistwd.html.

Mölnlycke Healt Care's Business Area Wound Care Global, Safetac technology, Silicone.

Mölnlycke Healt Care's Business Area Wound Care Global, Safetac technology, Safetac technology.

Mölnlycke Healt Care's Business Area Wound Care Global, Mepilex.

Thomas, Steve, Ph.D., "Soft silicone dressings: frequently asked questions", World Wide Wounds, www.worldwidewounds.com/2003/october/Thomas/Soft-Silicone-FAQ.html.

Tendra, mepilex border.

Tendra Open Wound Care System, tendra mepilex transfer.

Thomas, David R., MD, "Prevention and treatment of pressure ulcers: What works? What doesn't?", Cleveland Clinic Journal of Medicine, vol. 68, No. 8, Aug. 2001, pp. 704-722.

Thomas, Steve, Ph.D., "Atraumatic dressings", World Wide Wounds, www.worldwidewounds.com/2003/january/thomas/atraumatic-dressings.html.

Tendra Open Wound Care System, mepilex border.

Versiva, Instructions for Use.

Versiva, "Innovative Moisture Management", downloaded Jan. 16, 2004 at http://www.convatec,com/versiva/us/three_proven_tech.htm.

Cica-Care*, Instructions for Use, downloaded Nov. 13, 2002 at http://wound.smith-nephew.com/us/wound/ProductDetail.asp?UniqueID = 0%2E9% . . . .

Smith & Nephew—Allevyn Adhesive, downloaded Jan. 16, 2004 at http://wound.smith-nephew.com/us/Product.asp?NodeID = 452 &UniqueID = 0.9.393 . . . .

Smith & Nephew—Allevyn Technology, downloaded Jan. 16, 2004 at http://wound.smith-nephew.com/us/Standard_asp?NodeID = 2711&UniqueID = 0.92594 . . . .

"Silicone Gel Breast Implants", The Report of the Independent Review Group, What is silicone?; downloaded on Jan. 27, 2005 at http://www.silicone-review.gov.uk/silicone/index.htm.

"Silicone Chemistry Overview", pp. 1-12, 1997, Dow Corning Corporation.

Bentley, David, "A Primer on How to Put Substrates Together" Paper, Film & Foil Converters, downloaded on Jan. 27, 2005 at http://pffc-online.com/unprinted_rolls/paper_coatinglaminating/.

Donatas Satas, ed., Advances in Pressure Sensitive Adhesive Technology 2, pp. 724-746. 1995.

* cited by examiner

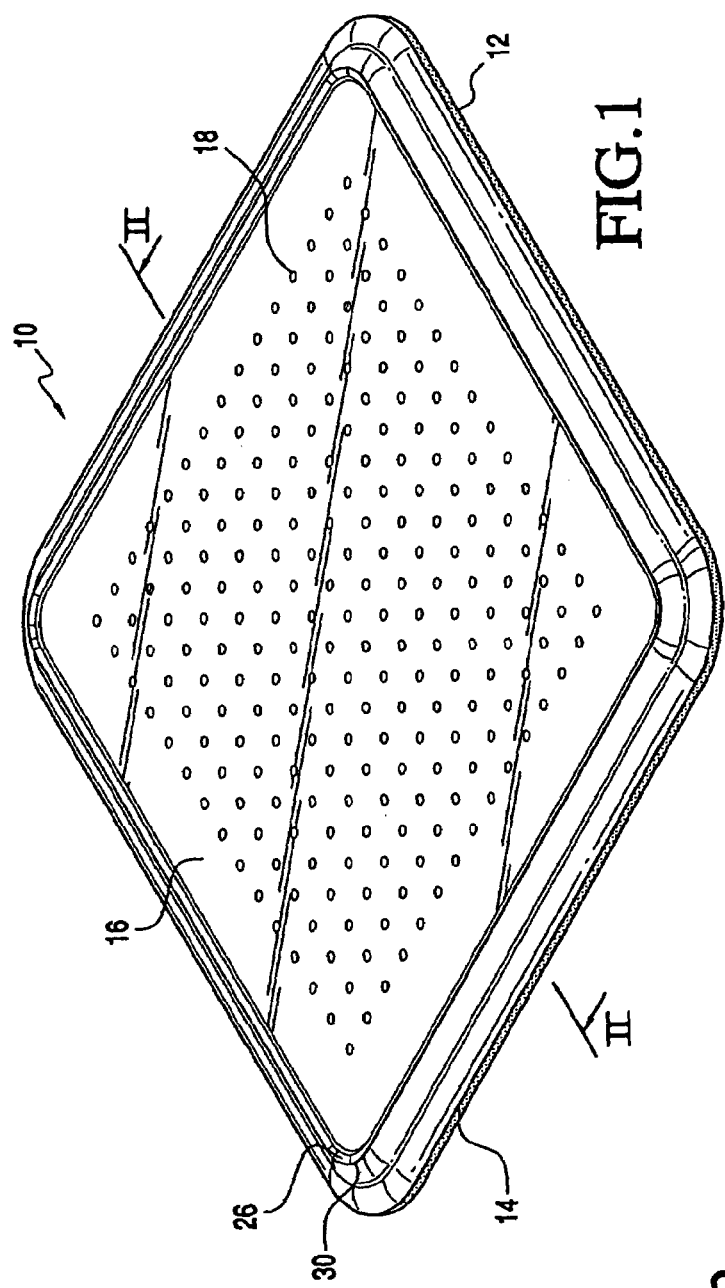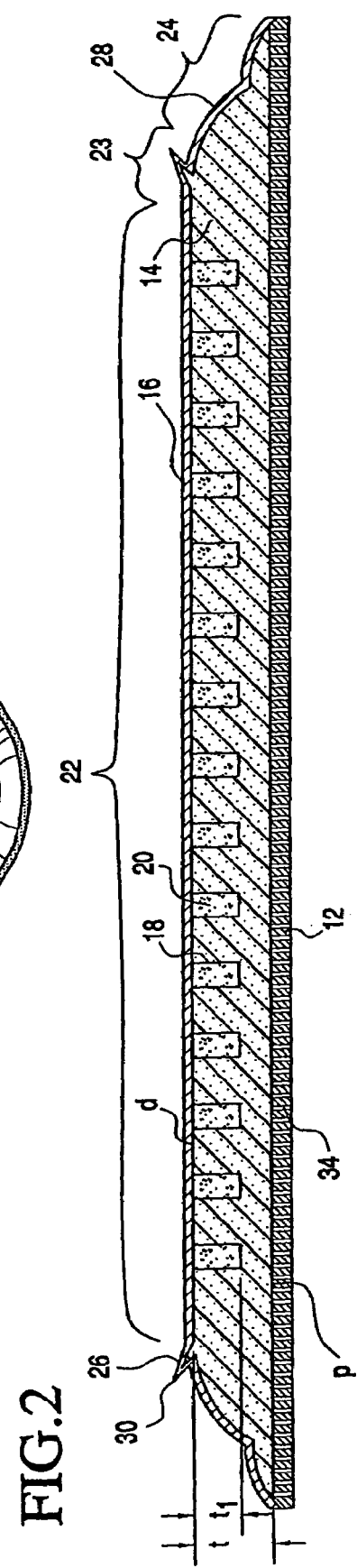

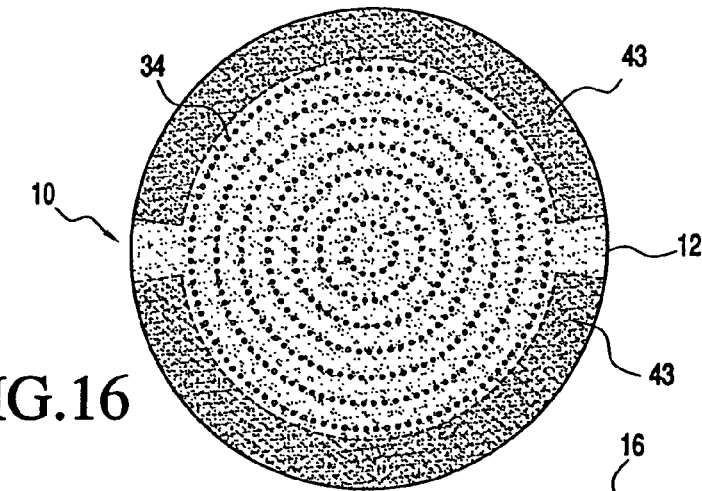
FIG.16
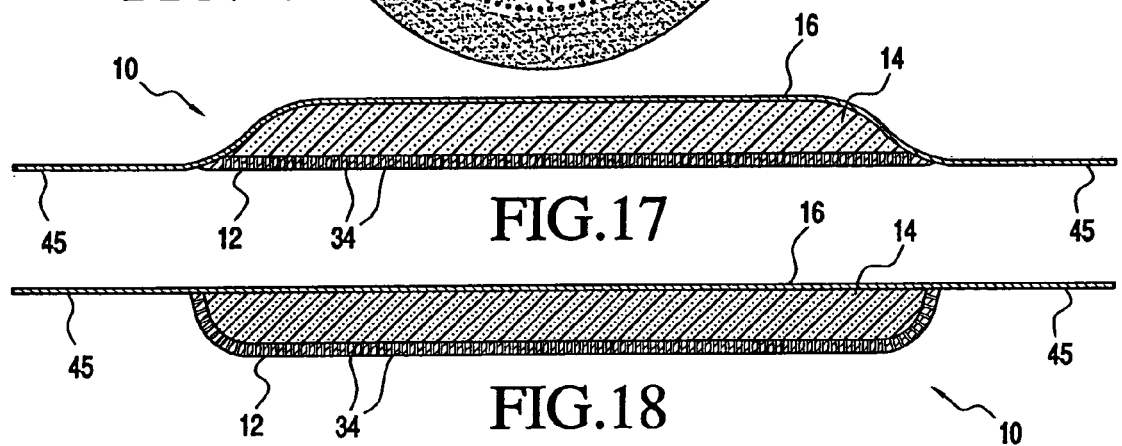
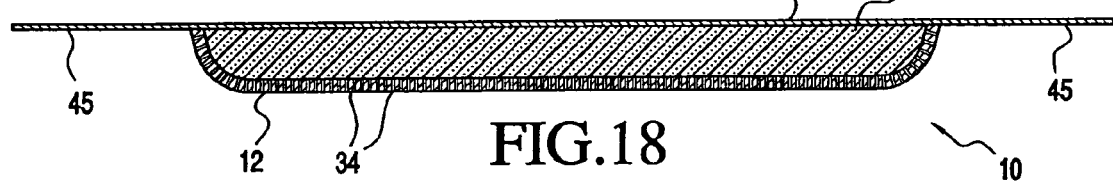
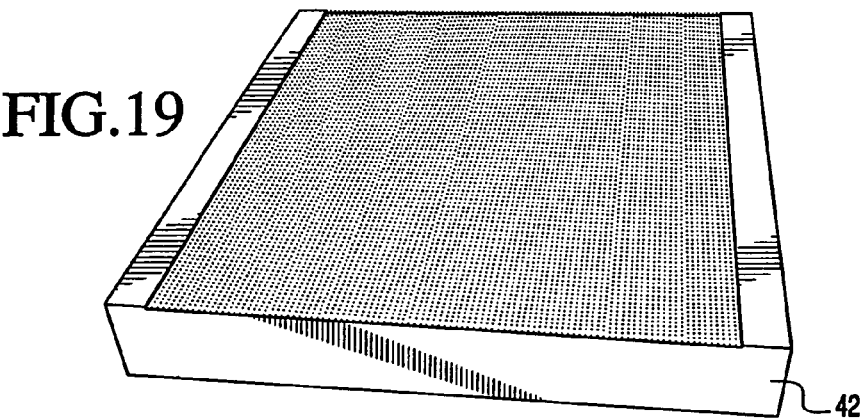
FIG.19
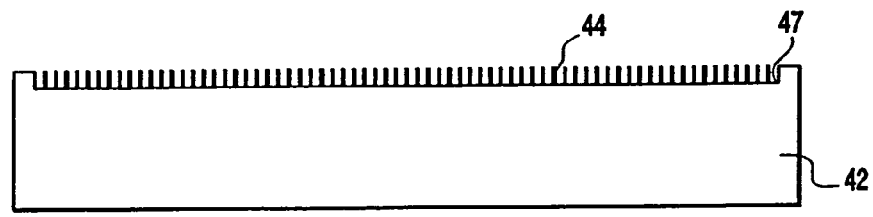
FIG.20

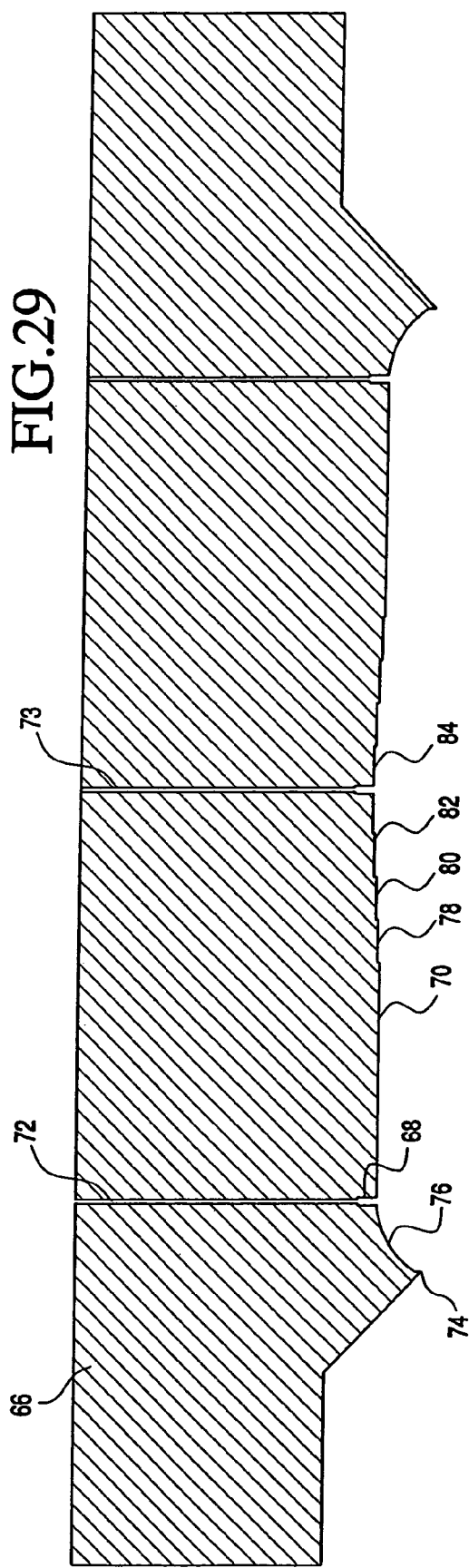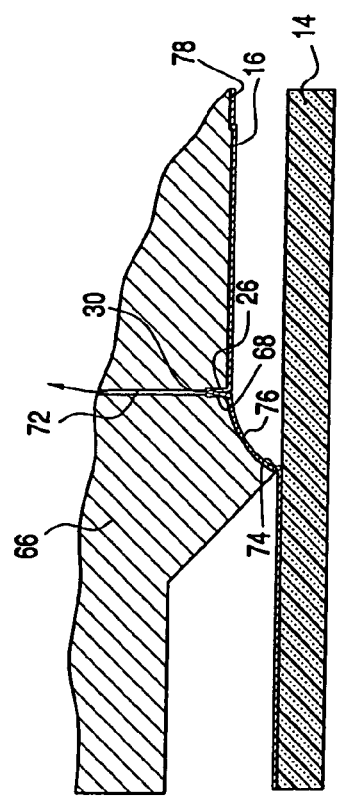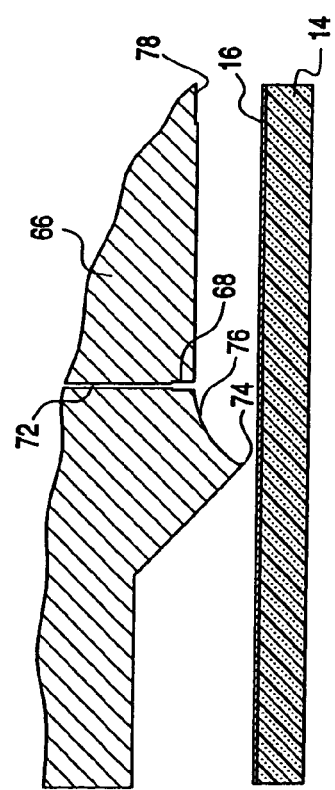

WOUND DRESSING

This application claims the benefit of U.S. Provisional Application Nos. 60/437,146 filed 31 Dec. 2002, 60/482,775 filed 27 Jun. 2003, 60/503,546 filed 17 Sep. 2003, and 60/518,317 filed 10 Nov. 2003.

BACKGROUND OF THE INVENTION

1. Field of the Invention

The present invention relates to a wound dressing, and more particularly to a wound dressing having a construction with improved skin adherence and absorptive capabilities, and methods for producing the same.

2. Discussion of Related Art

Historically, many diverse materials of various origins have been used to treat wounds by absorbing wound fluids and tissue, hereinafter generally referred to as exudate, from a wound site with some type of absorbent material. In recent years, use of polymeric-based wound care products have become increasingly popular to control wound site environmental factors such as water vapor, oxygen permeability, bacterial impermeability, and absorption of exudate. Such wound care products are tailored to meet specific requirements including conformability to a body portion, selective adherence to a wound bed, and adhesiveness to the skin surrounding the wound site.

Recently, occlusive or moisture-retentive dressings have gained increasing acceptance in treating wounds, in particular pressure sores and ulcers. A wide variety of types of structures are known in the art for use in or as occlusive dressings and generally comprise components for receiving, absorbing and retaining exudate. Typically, these wound care products include polymeric foams, polymeric films, particulate and fibrous polymers, hydrogels and hydrocolloids. Dressings with at least one of these components promote wound healing by providing a moist environment, while removing excess exudate and toxic components, and further serve as a barrier to protect the wound from secondary bacterial infection. While these known occlusive wound dressings can effectively manage a wound, many have been found to possess certain limitations or disadvantages.

In wound care, one of the main objectives of a wound dressing is to increase, improve or maximize utilization of the absorbent capacity of the dressing so as reduce or eliminate maceration, and facilitate the healing process of the wound. The control of exudate is of prime importance if a moist wound microenvironment is to be maintained. Unfortunately, many wound dressings have been found to remove all the exudate that a wound produces, thereby causing a "dry" wound that is undesirable in the wound healing process or in the alternative, such wound dressings have been found to absorb or control the exudate insufficiently, thereby leading to a pooling of the exudate which may increase the risk of bacterial proliferation and lead to infection.

Many wound dressings in the prior art include an absorbent layer having absorptive capabilities. Typically, the absorbent layer contains hydrophilic materials that absorb exudate and permit the wound dressing to be left in place for a period of days. Such absorbent layers may comprise a non-woven material or foam containing hydrocolloid particles such as the dressings described in U.S. Pat. Nos. 4,373,519 and 6,566,576, or a hydrophilic foam layer, such as in the dressings described in U.S. Pat. Nos. 5,409,472, 5,782,787, 6,040,492, 6,051,747, and 6,486,378.

While absorbent layer dressings are configured to absorb wound exudate, they often possess the disadvantage of being limited in the amount of exudate that may be absorbed. The limit to the maximum absorption of absorbent foam is often directly related to their geometrical size prior to absorbing a fluid. For example, hydrophilic foams may expand only to 12-15% of their original size. Another disadvantage is that it has been found that a certain amount of the exudate can be "squeezed" out of absorbent foam dressings due to poor liquid retention. The ability of exudates to be squeezed from the foam layer, and thus dressing itself, poses a risk of infection and may interfere with the healing of the wound.

Yet another disadvantage with known dressings is that absorption of exudate by an absorptive layer in contact with the wound causes the central portion of the applied dressing to swell and push up against the wound. Continued swelling can induce separation of the skin adherent layer from the skin outside the wound area, especially at the border of the wound dressing whereat a "curling" effect may occur. This excessive swelling of the wound dressing may further lead to leakage of the exudate from the periphery of the dressing, thereby providing a tract for the invasion of pathogenic microorganisms and further promoting maceration of the wound site.

Conventionally, a backing layer is provided that comprises a liquid impervious film that is attached to the absorbent layer to prevent exudate from seeping from the dressing. A difficulty arises during fluid uptake in that as the absorbent core expands, the backing layer must accommodate the expansion of the absorbent layer without causing curling of the dressing. An attempted solution to this problem is described in U.S. Pat. No. 4,738,257 which discloses a backing layer formed of a thin elastic sheet which is yieldable as the absorbent core swells. It has been found, however, that a liquid impervious plastic film cannot be made to sufficiently stretch in keeping with the expansion of the absorbent layer, and as a result, the film counteracting with the swelling absorbent layer may produce the aforesaid curling at the border of the dressing. Another proposed solution is provided in U.S. Pat. No. 6,040,492 which discloses a wound dressing that includes a backing layer that is attached to an absorbent foam core and includes a plurality of wrinkles that substantially flatten as the foam core swells. While the backing layer may accommodate the expansion of the foam core, the fluid uptake of this wound dressing is limited by the expandability of the foam core itself. Accordingly, due to the limited absorptive capacity of the foam core, the dressing must be replaced often.

Ideally, a wound dressing must be adhesive in nature such that it may attach to the wound site while being non-toxic and eliciting no more than a minimal allergenic response. Moreover, a wound dressing should possess the ability to prevent bacteria from entering the wound from the ambient environment while providing a suitable moisture transmission rate.

It has been found, however, that many known occlusive dressings possess the disadvantage of relying solely on a pressure sensitive adhesive layer that is used to secure the dressing to skin, for instance an acrylate glue having a high specific adhesiveness. Typically, a wound dressing with only an adhesive has a tendency to strip the central portion of the dressing from the wound when removed from the wound and thus may damage healing tissue.

Wound dressing have been commercially available that include an absorbent foam core with a wound contacting surface coated with a layer of silicone gel. The silicone gel randomly lines portions of the walls of the pores of the absorbent foam to form a plurality of randomly formed apertures. These apertures are formed by capillary action when an uncured silicone gel is applied to the foam core. One drawback to this approach is that the silicone gel may close some of the pores, and another drawback is that the holes are randomly formed which may lead to localized areas that inhibit the uptake of the exudate into the foam core. While in some applications it may be desirable to provide the wound dressing with a greater concentration of apertures at selected regions of the wound dressing to increase exudate uptake at such areas, this approach does not accommodate such a formation of a predetermined pattern of apertures. Furthermore, another drawback to this approach is that the surface roughness of the silicone layer is largely dependent upon the surface of the foam to be coated, and in the event it is desired to obtain a smooth silicone layer to be worn on the skin, this approach fails to yield such a smooth silicone layer.

Developments in the field of silicone manufacturing have led Ossur hf of Reykjavik, Iceland, and assignee of the present invention, to produce silicone products adapted for skin contact that provide superb softness, gentle skin contact, and may include unique skin care ingredients. In particular, such silicone manufacturing has led to advances in improved comfort and cushioning of prosthetic suspension liners that have excellent durability and intimacy using proprietary silicone technology of Ossur hf. It has been found that by applying the silicone technology of Ossur hf to produce an ultra-thin, perforated tacky silicone sheet, a silicone adhesive layer can be produced that possesses superior gentle adherence to wound sites while not damaging skin and the wound bed due to single or repeated removal of the silicone layer.

Despite the availability of a variety of absorbent wound dressings, there is a need and a demand for an improved wound dressing which prevents wound trauma upon wound dressing changes, improves the durability and lifetime of the wound dressing, anatomically conforms to a wound and possesses improved fluid uptake, retention and removal properties. Most importantly, it is desired to produce a wound dressing having an adhesive layer that does not possess the drawbacks of known adhesive layers, and instead, gently adheres and detaches from a wound site while providing superior fluid uptake. Moreover, there is a need and a demand for an improved method of forming such an improved wound dressing that is both simple and cost effective.

SUMMARY OF THE INVENTION

The present invention is directed to an improved wound dressing possessing superior absorbent capabilities including increased fluid uptake and enhanced retention properties. In an embodiment of the invention, a wound dressing includes a skin adherent facing layer comprising a discrete layer of silicone gel having a plurality of preformed apertures arranged in a pattern. In another embodiment of the invention, the wound dressing includes a skin adherent facing layer having a discrete layer of silicone gel including a plurality of preformed apertures arranged in a pattern. In yet another embodiment, the facing layer includes at least two different discrete layers of silicone gel.

Embodiments of the invention include various configurations of the pattern of the apertures, such as patterns wherein the apertures have different shapes, densities along varying regions of the facing layer, alternating sizes, and different spacing arrangements.

The skin adherent, facing layer employs the silicone technology and know-how of Ossur hf. The silicone gel layer has properties that permit the gel to adhere gently to surrounding skin at the wound site. The silicone gel layer is inherently soft to the touch and flows partly into microscopic cavities and cracks in the skin when applied thereon to create a large contact area over the wound site.

Numerous other advantages and features of the present invention will become more readily apparent from the following detailed description of the invention, the accompanying examples, drawings and the appended claims.

BRIEF DESCRIPTION OF THE DRAWINGS

FIG. 1 is a perspective view of an embodiment of a wound dressing of the invention;

FIG. 2 is a sectional view of the wound dressing along line 11-11 in FIG. 1;

FIGS. 14-16 are plan views showing embodiments of facing layers having regions with different degrees of skin adherence of the invention;

FIGS. 17-18 are elevational views showing embodiments of a backing layer having a skin adherent border section of the invention;

FIG. 19 is a perspective view of an embodiment of a perforation plate for forming apertures in a facing layer of the invention;

FIG. 20 is an elevational view showing the perforation plate of FIG. 19;

FIG. 29 is a cross-sectional view showing an embodiment of a platen used to apply a backing layer to an absorbent core of the invention; and FIGS. 30-34 are schematic views showing an arrangement for applying a backing layer to an absorbent core of the invention.

DETAILED DESCRIPTION OF THE PREFERRED EMBODIMENTS

Figure 3:
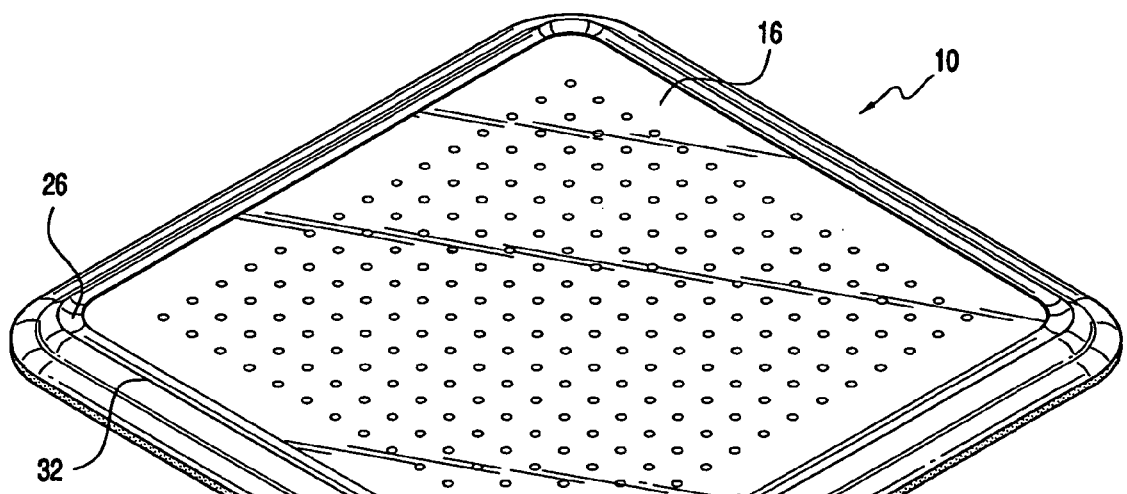
FIG. 3 is a perspective view of an embodiment of a wound dressing of the invention.

As shown in FIGS. 1 and 2, the wound dressing 10 of the present invention preferably includes a perforated hydrophobic, skin adherent facing layer 12, an absorbent core 14, and a liquid impervious, moisture permeable backing layer 16. The wound dressing depicted in FIG. 1 is in a dry state substantially devoid of moisture. As more fully exemplified in FIG. 2, the absorbent core 14 defines a proximal surface p that is intended to face towards a wound surface and a distal surface d that is opposed to the proximal surface p and faces away from a wound surface. In a basic configuration, the dressing 10 comprises the facing layer 12 secured to the proximal surface p of the absorbent core 14 and the backing layer 16 attached and sealed to at least part of the distal surface d of the absorbent core 14.

In a preferred embodiment, the absorbent core 14 defines a plurality of receptacles 18 arranged in a predetermined pattern wherein the receptacles 18 are defined as a repeating series of cylindrical compartments. As shown in FIG. 2, the receptacles 18 open at the distal surface d of the absorbent core 14 and extend a distance into the absorbent core 14 a distance $t_1$, short of its entire thickness t. The receptacles may assume a variety of configurations and may be cylindrical in shape, extend transversely along at least a portion of the distal surface of the absorbent core, or assume other possible configurations as will be discussed below. The plurality of receptacles 18 contain discrete portions of absorbent material 20 that absorb exudate from the wound and migrate from the receptacles 18 towards the backing layer 16 upon absorption of such exudate.

As illustrated in FIG. 2, the absorbent core 14 generally defines central, intermediate and border portions 22, 23, 24. Preferably, the backing layer 16 is secured to the border portion 24 of the absorbent core 14 and sealed along its periphery. The border portion 24 preferably includes a bevel 28 defined near or along a peripheral edge thereof and is provided to retain any loose absorbent material 20 from the receptacles 18 within the dressing 10. As will be discussed more fully below, the backing layer 16 is preferably lightly adhered to the central portion 22 of the absorbent core 14 when the dressing 10 is in a dry state.

The backing layer 16 of the dressing 10 preferably includes a compliant element 26 that is interposed between the central and border portions 22, 24 of the absorbent core 14. The compliant element 26 is generally concentric with the central portion 22 and comprises a portion of the backing layer 16 that may not be adhered to the absorbent core 14 when the dressing 10 is in a dry state. Preferably, the compliant element 26 includes at least one concentric ridge. While FIG. 2 shows the dressing 10 with a compliant element 26 having only one concentric ridge 30. FIG. 3 illustrates a dressing 10 having a plurality of ridges wherein inner and outer ridges 31, 32 extend outwardly from the distal surface d of the absorbent core 14, and generally constitute inner and outer boundaries of the compliant element 26.

It will be understood that the compliant element may assume a variety configurations. For example, the orientation of the compliant element may be arranged in a variety of directions such as the ridge extending in a range of directions from being generally parallel to the absorbent core on the border portion side of the compliant element to being generally parallel to the absorbent core on the central portion side of the compliant element.

Figure 5:
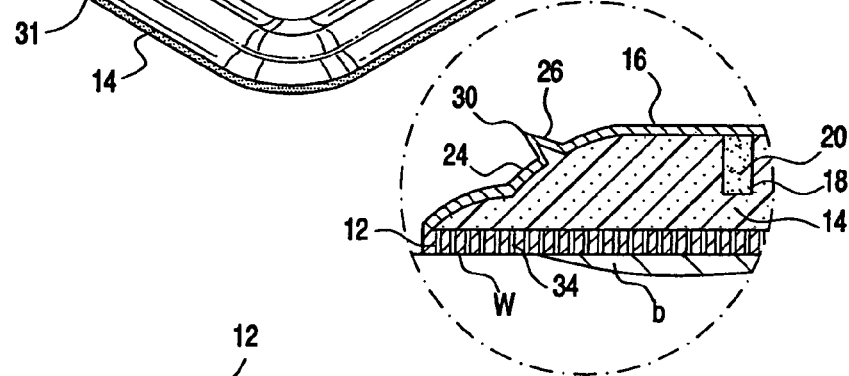
FIG. 5 is an enlarged view of a section of another embodiment of the wound dressing in FIG. 2.

As shown schematically in FIG. 5, the compliant element 26 is not limited to being positioned generally along the intermediate portion of the absorbent core. The compliant element 26 may be positioned on the border or the central portions of the wound dressing wherein the compliant element 26 may include at least one ridge 30 or segment thereof on at least one of the border or central portions of the wound dressing. Such adaptation of the wound dressing to include a compliant element on at least one of the border or central portions of the wound dressing may be provided to improve the expandability and distension of the backing layer relative to the distal surface of the absorbent core.

Figure 4:
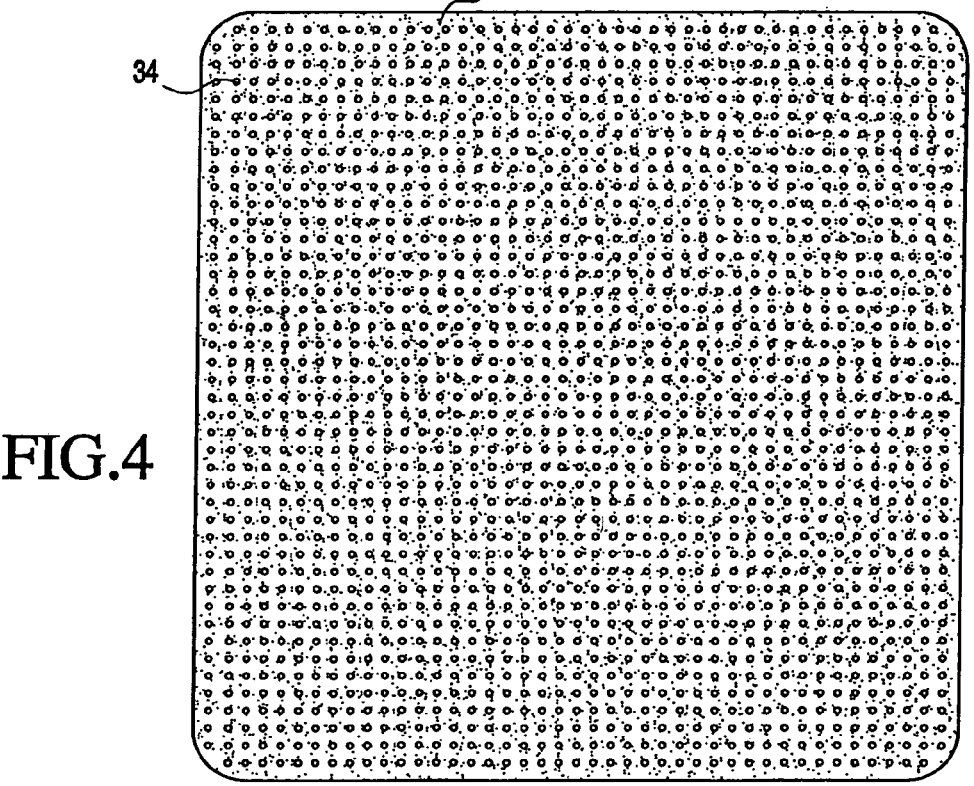
FIG. 4 is a plan view showing an embodiment of a facing layer of the invention.

The facing layer 12 is preferably secured to the proximal surface p of the absorbent core 14. The facing layer 12 includes a plurality of apertures 34 that are preformed in a pattern prior to securing the facing layer 12 to the absorbent core 14. As shown schematically in FIGS. 2 and 4, the plurality of apertures 34 may be arranged in a predetermined pattern. The plurality of apertures 34 may be configured to correspond to regions near or at the plurality of receptacles 18 of the absorbent core 14 so as to transport exudate from a wound site to the absorbent core 14. The facing layer 12 is preferably secured only to the proximal surface p of the absorbent core 14 and preferably does not coat the walls of the pores or holes of the absorbent core 14 defined near the proximal surface p thereof. It will be understood, however, that portions of the facing layer may fill irregularities disposed along the proximal surface of the absorbent core or pores of the absorbent core so as to improve the security of the facing layer to the absorbent core.

Figure 6:
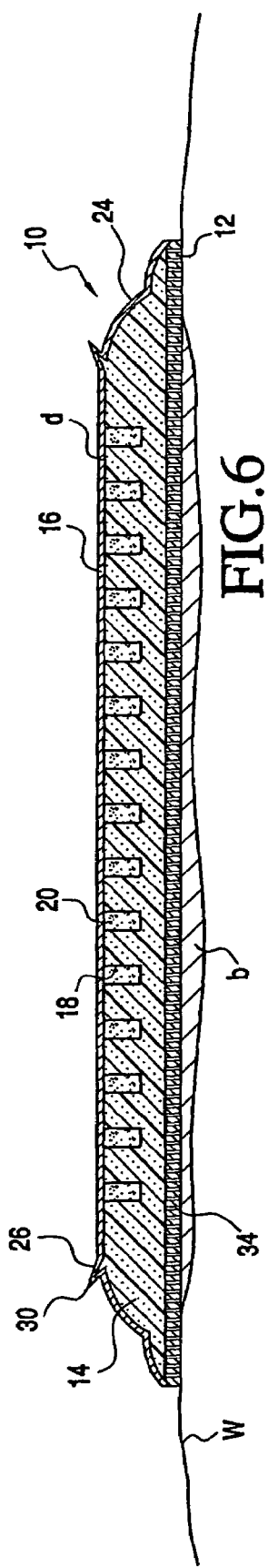
FIGS. 6-8 are sectional views illustrating progressive swelling of the wound dressing in FIGS. 1-2 over a wound site.
Figure 7:
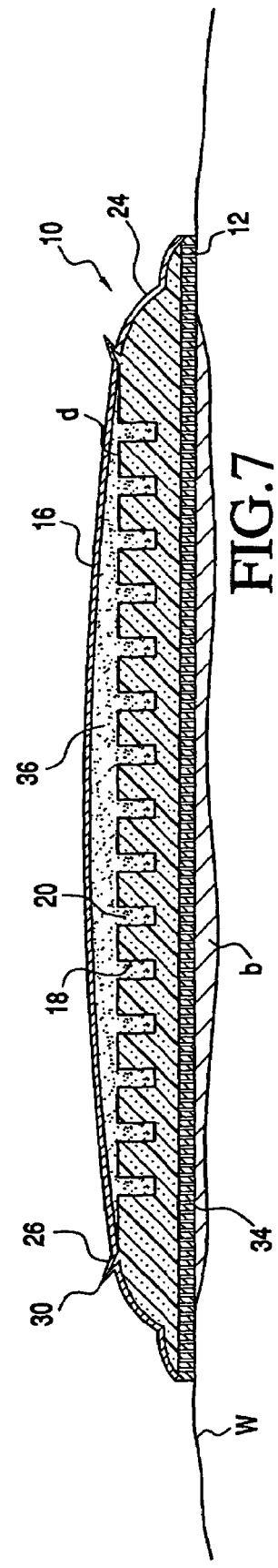
Figure 8:
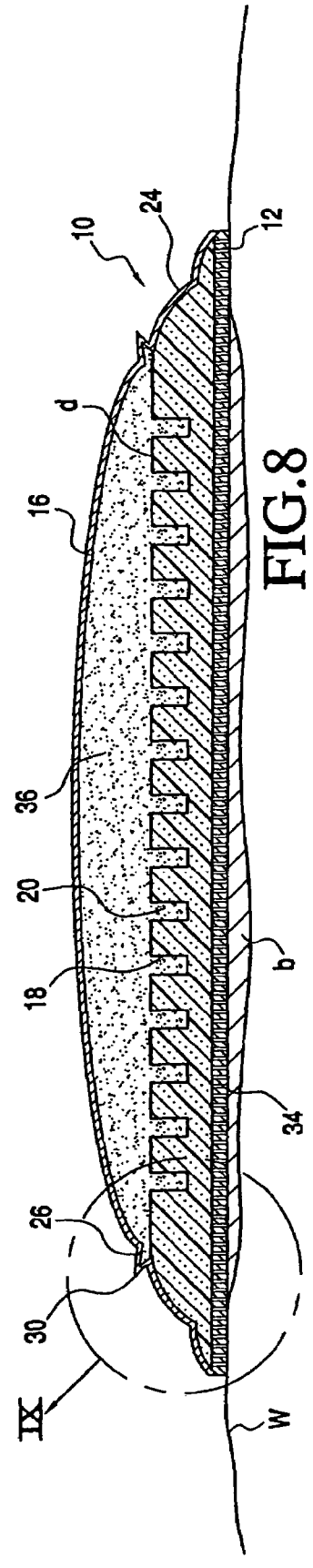

While not wishing to be bound by a particular mechanism of operation, the present invention is intended to function as a dressing 10 in the manner depicted in FIGS. 6 to 8, after application of the dressing to a fluid-exuding skin wound. It will be understood that in the context of the invention, the terms fluid, moisture and exudate are used interchangeably regarding wounds and wound dressings. The dressing 10 is placed onto a wound site w with the facing layer 12 directed over the wound bed b. The facing layer 12 may adhere to the intact skin around the wound site w as well as to the wound bed b. The dressing 10 is maintained in close apposition to the wound bed b in part by the capillary action of the exudate entering the absorbent core 14 and by the facing layer 12.

As illustrated in FIG. 6, fluid exuded by the wound bed b will be drawn through the apertures 34 towards the absorbent core 14, and the absorbent material 20 contained in the receptacles 18. After being applied over the wound site w for an extended period of time, the applied dressing 10 may appear as shown in FIG. 7 with a slightly enlarged domed, reservoir configuration 36 extending over the central portion of the absorbent core 14. The reservoir 36 is caused by the absorbent material 20 that has absorbed a desired quantity of exudate from the receptacles 18 and discrete portions thereof have swelled and migrated from the receptacles, thereby causing distension of the backing layer 16. The swollen exudate-laden discrete portions of absorbent material 20 cause the backing layer 16 to detach from the distal surface d of the absorbent core 14 in a predictable manner and to distend upwardly to further permit continued absorbing and swelling of the dressing 10 over the wound site w. In addition, the absorbent core 14 will expand or swell both transversely and longitudinally, and the area of absorbent core 14 will generally increase with increased fluid absorption.

While the backing layer 16 remains sealed along the border portion of the dressing 10, the reservoir 36 is formed such that it is defined between the backing layer 16 and the distal surface d of the absorbent core 14, and sealed along the border portion 24. The reservoir 36 permits the migration of the swollen discrete portions of absorbent material 20 from the receptacles 18 and greatly expands the retention of fluid from the wound bed b. The compliant element 26 effectively functions as a flexible joint for the backing layer 16 by permitting additional expansion of the backing layer 16 in providing additional flexibility and expansion of the backing layer 16 due to the swelling of the absorbent material 20. As shown in FIG. 8, the dressing 10 has nearly reached its swelling capacity and the backing layer 16 has distended to its maximum.

Most notably, at this advance stage of swelling, the border portion 24 of the dressing 10 remains attached to the wound site w due to the provision of the compliant element 26 which compensates for the expansion and swelling of the absorbent core 14 and the absorbent material 20, and the distension of the backing layer 16. It will be further noted that the ridge 30 generally does not fully flatten relative to adjacent portions of the backing layer 16 and generally extends outwardly, at least in part, from the distal surface d of the absorbent core 14 and in relation to the distended portion of the backing layer 16 delimited by the compliant element 26.

It will be understood that the preferred facing layer 12 also has suitable elastic properties to enable it to stretch as the absorbent core 14 expands laterally.

Figure 9:
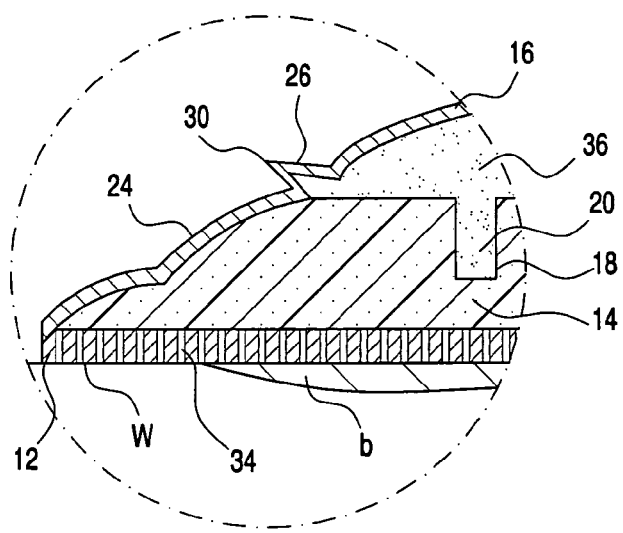
FIG. 9 is an enlarged view of a section of the wound dressing in FIG. 8.

When the dressing 10 has expanded to a maximum capacity, defined as an exudate-laden or fully saturated dressing, it will be desirable to remove and replace the dressing 10. When in a saturated or fully exudate-laden stage, the corners along the border portion 24 of the dressing 10 generally remain adhered to the wound site w despite the excessive uptake of exudate, as exemplified in FIG. 9, since the facing layer 12 provides sufficient adherence to the skin surrounding the wound site w. By observing the extent of swelling of the dressing in relation to the degree of fluid uptake into the absorbent core and by the absorbent material, one can be visually determine when it is appropriate to remove the dressing.

Figure 10:
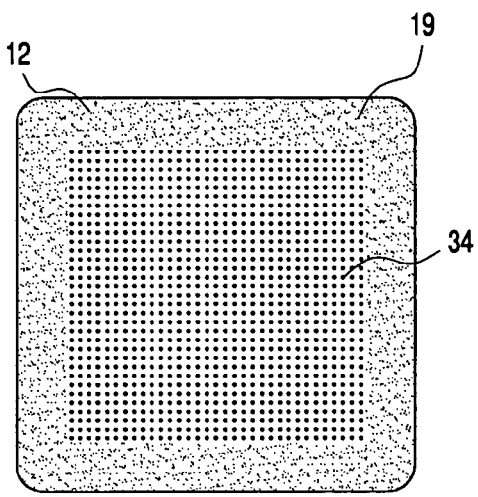
FIG. 10 is a plan view showing an embodiment of a facing layer of the invention.

As exemplified in FIG. 10, the dressing 10 may include an additional adhesive 19 disposed on the facing layer 12. Preferably, the adhesive 19 is deposited on the facing layer 12 at or near a portion corresponding to the border portion of the absorbent core 14. The pressure sensitive adhesive 19 is preferably a tacky pressure sensitive silicone or an acrylate adhesive known in the art of wound dressings.

In a preferred embodiment, the absorbent core 14 comprises preferably a hydrophilic synthetic polymer conformable to body surfaces and adapted to be capable of absorbing fluid. It is desirable that the absorbent core absorb exudate rapidly so as to enhance its effectiveness in the dressing of the invention, and in particular, the fluid uptake to the receptacles containing the absorbent material. In addition to absorption, an effective wicking mechanism is desirable, that is the absorbent core should rapidly direct fluids away from the proximal surface of the absorbent core to more remote areas for storage (i.e., the receptacles containing the discrete portions of absorbent material), so as to minimize local saturation and maximize the efficiency of the absorbent core.

Figure 12:
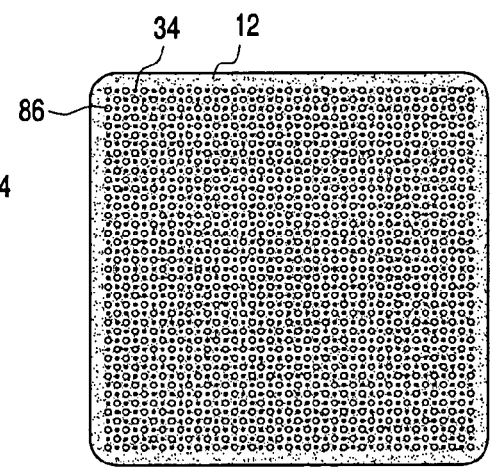
FIG. 12 is a plan view showing an embodiment of a facing layer of the invention.

In an exemplary embodiment, FIG. 12 shows how the facing layer 12 may be configured to have different sized apertures 34, 86. According to this embodiment, the apertures are arranged in rows wherein the large apertures 86 alternate with the smaller apertures 34.

A preferable absorbent core is constructed of flexible open-cell foam that is at least slightly hydrophilic. Suitable foams have an open cell size of 30 to 700 microns, and preferably a cell size of 50 to 300 microns. The open cells permit transport of fluid and cellular debris into and within the foam, and it preferred that the cell size of areas of the foam be of sufficient size to encourage capillary action and promote fluid transport.

The absorbent core may expand about 135% of its size when saturated with fluid. When combined with the facing and backing layer of the invention, the absorbent core may expand to only about 110% of its dry size when exudate laden.

In accordance with one embodiment of the invention, the absorbent foam comprises a gradient of cell sizes across the thickness of the absorbent core such that the cell size decreases in the direction of the distal surface and of the absorbent core. Since the cell sizes are greater at and near the proximal surface of the absorbent core, the capillary forces are stronger and therefore will drain fluid near the proximal surface of the absorbent core and draw the fluid towards the receptacles. In addition, the absorbent foam may include a cell size gradient that is directed towards the receptacles, thereby providing localized regions in the absorbent foam that are configured to have increased capillary forces directed towards the receptacles to aid in the guidance of fluid thereto.

The foam may be made, for example, from polyurethane, cellulose, carboxylated butadiene-styrene rubber, polyester foams, hydrophilic epoxy foams or polyacrylate. In a preferred embodiment, the foam is formed from hydrophilic polyurethane foam, such as polyurethane foam made by Reynel Inc. (Boothbay, Me.) under product designation L00562-B. Since the aforesaid foams are hydrophilic per se and further in view of the use of the receptacles containing absorbent material, it is not necessary to treat the foams to render them more hydrophilic in a preferred embodiment.

In another embodiment, if desired, the foam may be treated so as to be more hydrophilic and therefore increase the tendency of the exudate to coagulate more rapidly in the foam, yet only to the extent that the foam is not too hydrophilic so that the hydrophilic properties of the foam prevents transport of the exudate to the absorbent material. In such an embodiment, the level of hydrophilic properties of the absorbent foam may be designed such that the surface tension is minimized to allow the easy passage of fluid into foam cells. The fluid is thus retained in the absorbent foam while maintaining a high relative humidity at the wound site.

It will be understood that the absorbent core is not limited to being constituted of foam. In another embodiment, the absorbent core may be a porous woven or non-woven material that may be produced by any number of means using known materials available to those skilled in the art. For example, the absorbent core may exist as a bulky, loosely formed web composed of very short cellulose fibers arranged in a random or non-random array, a pad of cellulose flakes, chitosan flakes, or a polymeric fibril matrix.

The thickness of the absorbent core will range from 0.5 mm to 20 mm, and is preferably between 3 mm to 5 mm.

The absorbent core may include an array of receptacles formed therein and may be defined in any suitable preselected pattern that can contain a desired bulk or quantity of discrete portions absorbent material, while maintaining sufficient strength and flexibility suitable for a dressing of the invention. In a preferred embodiment shown in FIG. 1, the pattern of the receptacles 18 is in a grid-like configuration. Preferably, such receptacles have a uniform, predetermined shape and size, and extend across the distal surface d of the absorbent core. In this embodiment, the receptacles are positioned in a rectangular pattern, and the receptacles are generally spaced apart 5 mm (measured from the center axis of each receptacle). The depth of each receptacle is generally 4-5 mm, and positioned at least 0.5 mm from the facing layer. In this embodiment, the pattern may be tailored to include more receptacles at specific regions of the dressing as opposed to other regions.

Figure 11:
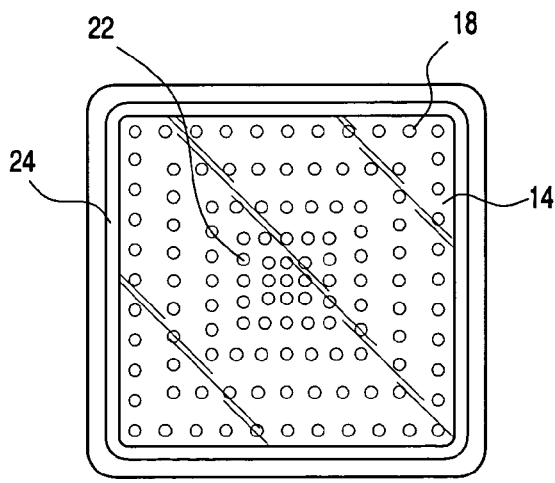
FIG. 11 is a plan view showing an embodiment of receptacles of an absorbent core of the invention.

In an embodiment of the wound dressing shown in FIG. 11, there is a higher density of receptacles 18 at the central portion 22 of the absorbent core 14 than near the border portion 24 of the dressing 10. The amount of receptacles at any given region of the absorbent core may be dependent upon the perceived areas of a greater amount of local occurrence of fluid, such as at the central portion, to maximize fluid absorption, and further limit the absorption of fluid at certain areas of the absorbent core such as at the border portion.

As shown in FIG. 2, the receptacles 18 are arranged to open at the distal surface of the absorbent core 14 and extend a distance into the entire thickness thereof. In a preferred embodiment, the receptacles extend a distance $t_1$, short of the entire thickness t of the absorbent core 18, and it is preferred that the receptacles extend a distance 70-90% of the total thickness of the absorbent core 14. It will be understood, however, that in an embodiment of the wound dressing, the receptacles may extend through the entire thickness of the absorbent core.

Figure 13:
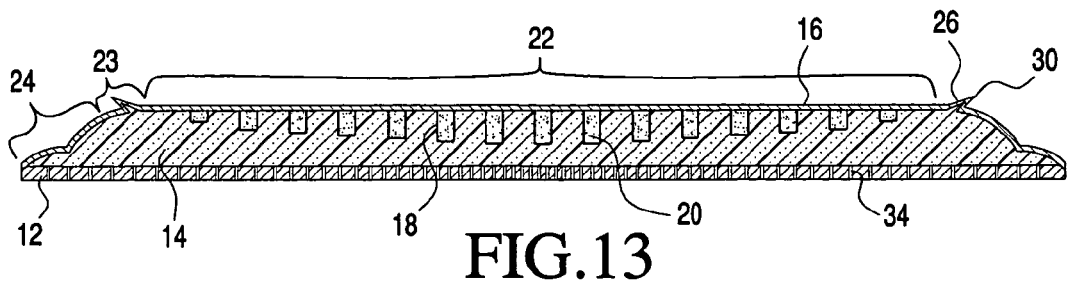
FIG. 13 is an elevational view showing another embodiment of receptacles and a facing layer of the invention.

In another embodiment of the wound dressing, the receptacles 18 may be arranged, as shown in FIG. 13, to extend at different distances into the thickness of the absorbent core 14 on the basis of their location and the local occurrence of fluid exuded from a wound site. In this embodiment, the receptacles 18 located closer to the center of the dressing 10 extend deeper into the thickness of the absorbent core 14 whereas the receptacles 18 closer to the border 24 of the absorbent core extend a shallower distance into the thickness of the absorbent core 14 than the receptacles 18 at the central portion 22. It follows that the deeper receptacles 18 will contain more absorbent material 20 than the shallower receptacles 18, and therefore provide a greater localized region of absorption.

Since the receptacles preferably extend only partly into the total thickness of the absorbent core, exudate will be transported to and absorbed by the absorbent material. This effect leaves the proximal side of the absorbent core without the receptacles in a desirably moist environment without excessive saturation of exudate and thus permits the dressing to remain on the wound site for a longer period of time.

In a preferred embodiment shown in FIGS. 1 and 2, the shape of the individual receptacles 18 is uniform and generally cylindrical. The shape of the receptacles is at least partly chosen to maximize the containment of the discrete portions of absorbent material and to facilitate the migration thereof when swollen by fluid. The receptacles are not limited to a cylindrical configuration; the receptacles may take on the shape of pyramids, channels, hemispheres, cones, blocks and truncated variations and combinations thereof. Moreover, the receptacles may include a taper extending from their opening to their base portion so that the receptacles have a greater width near the opening than at the base portion. This configuration facilitates migration of swollen, moisture-laden discrete portions of absorbent material from the receptacles so that they can flow more freely from the receptacles. Alternatively, the receptacles may be arranged in a random pattern along a transverse direction of the distal surface of the dressing.

In an embodiment of the absorbent core, the receptacles may comprise a plurality of channels extending transversely along at least a portion of the distal side of the absorbent core. In this embodiment, the channels may have a denticulate or an undulating cross-sectional profile. This embodiment may be useful in a wound dressing wherein the absorbent core is too thin to include receptacles having a form such as the aforesaid cylindrical receptacles.

The size of the individual receptacles may be of any suitable size that will contain a suitable amount of absorbent material that will sufficiently absorb exudate from a wound site. Generally, the receptacles are sized from about 500 to 5,000 micrometers, preferably about 1000-3000 micrometers in cross-section (independently height and width dimensions). The receptacles in a preferred pattern have a repeat distance defined as the distance from one receptacle to the next receptacle, center axis to center axis, of 500 to 5,000 micrometers, preferably about 1000-4500 micrometers.

While in a preferred embodiment the receptacles have a uniform volume across the transverse directions of the wound dressing, the receptacles may have varying volumes depending upon the location of their openings on the distal surface of the absorbent core. As with the embodiment related to the varying depths of the receptacles, the receptacles located at or near the central portion of the absorbent core may have greater volumetric capacity than the receptacles closer to the border portion of the absorbent core. It follows that the receptacles having varying volumes will likewise contain varying bulk amounts of discrete portions of absorbent material.

The absorbent material used in the dressing of the present invention is preferably comprised of superabsorbent polymeric granulates, flakes or powders that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, cross-linked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer. Superabsorbent particulate hydrophilic polymers also are described in detail in U.S. Pat. No. 4,102,340. That patent discloses absorbent materials such as cross-linked polyacrylamides. Preferably, the super absorbent particles used in the dressing of the present invention are preferably composed of cross-linked polyacrylic-acid.

Superabsorbent particles are available commercially, for example starch graft polyacrylate hydrogel powders are available from Hoechst-Celanese of Portsmouth, Va. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), and FAVOR (produced by Degussa AG, Dusseldorf, Germany).

The super absorbent particles are preferably in the form of granules or flakes to provide a greater available surface area hydrocolloid. The size of the super absorbent particles is typically within the range of 1 to 1000 micrometers when dry. Preferably, the particle size range of the absorbent particles is 100 to 900 micrometers. The particles which are insoluble in a wound environment have an absorptive capacity greater than 0.5 of water per gram of dry particles.

In another embodiment, the absorbent material may be a hydrophilic gel that swells upon contact with water. The hydrophilic gel generally lacks a cellular or voided internal structure, and is in the form of a solid or semi-solid. Hydrophilic gel may be construed to mean hydrocolloids, hydrogels and combinations thereof as long as the material is physiologically tolerable and clinically acceptable. A description of suitable hydrophilic gels is provided in U.S. Pat. No. 6,566,575 granted to Stickels et al. and such hydrophilic gels are commercially available.

In another embodiment of the wound dressing, the absorbent core may include a plurality of discrete portions of absorbent material enmeshed in the absorbent core. Such discrete portions of absorbent material may be discrete superabsorbent polymeric granulates, flakes or powders that are freely disposed in the absorbent core so that they may migrate within the absorbent core, and preferably towards the distal surface thereof. In yet another embodiment of the wound dressing, the absorbent core may include both absorbent material enmeshed therein and the receptacles containing discrete portions of the absorbent material.

In summary, in each of the absorbent core embodiments discussed thus far, it is notable that the absorption of the fluid at the portion of the absorbent core near or at its proximal portion is minimized, and the absorption of fluid is maximized by the absorption of the absorbent material at or beyond the receptacles. Such a mechanism maximizes the amount of fluid that the dressing can absorb, in combination with the configuration of the backing layer, and further allows longer wear time for the patient since the fluid is not in contact with the skin.

A backing layer may be present in all of the embodiments of the dressing of the present invention. Preferably the backing layer is conformable to animal (inclusive of human) anatomical surfaces, is impermeable to liquid and is vapor permeable. As discussed above, the backing layer, in combination with the absorbent core, may be constructed to define a reservoir therebetween when the dressing is in an expanded moisture-laden state. While the backing layer does not permit the passage of a liquid or exudate, moisture in the absorbed exudate passes through the backing layer in a vapor form into the atmosphere.

The preferred embodiment for the backing layer is a thin polymeric elastic or flexible film coating providing a bacterial barrier formed from a water vapor permeable pliable elastomer material. The film is continuous in that it has no perforations or pores which extend through the thickness of the film. Films of this type are known and generally are hydrophilic polymeric materials through which water vapor is capable of diffusing.

The backing layer is bonded to the proximal surface of the absorbent core, and in a preferred embodiment, the backing layer is bonded only to the distal surface of the absorbent core and does not penetrate any pores, cells or cavities therein. Generally, the film is 15 to 45 micrometers in thickness, with a preferred thickness of about 30 micrometers. The backing layer may comprise polyurethane, such as a polyurethane film available from InteliCoat Technologies (South Hadley, Mass.) under product designation INSPIRE, elastomeric polyester, blends of polyurethane and polyester, polyvinyl chloride, and polyether-amide block copolymer. The preferred backing layer for use in the present invention is a polyurethane film since it exhibits a resilient property that allows the film to have good conformability and further has a high degree of stretchability.

It is preferred that the backing layer of the present invention be at least translucent, and more preferably, sufficiently transparent so that the wound site to which the dressing is applied can be viewed through the dressing. It is advantageous to view to evaluate the wound and healing thereof without removal of the dressing to avoid unnecessary handling of the dressing and exposure of the wound to the environment, which reduces the likelihood of contamination.

Suitable continuous conformable backing layers will have a moisture vapor transmission rate (MVTR) of the backing layer alone of 1500 to 14600 g/m^2/24 hrs, preferably 2500 to 2700 g/m^2/24 hrs at 38° C. The backing layer thickness is preferably in the range of 10 to 1000 micrometers, more preferably 100 to 500 micrometers. The facing layer of the present invention is preferably a hydrophobic, liquid and moisture impervious layer bonded to the proximal surface of the absorbent core. In a preferred embodiment, the facing layer is a cross-linked silicone elastomer gel, such as, for example, a cross-linked silicone (polydimethyl siloxane gel) manufactured by NuSil Technology (Carpenteria, Calif.) under product designation MED-6340. The facing layer preferably has a thickness in the range of 0.05 mm to 0.5 mm, and more preferably 0.1 mm. The conformability of the dressing to the wound is somewhat dependent on thickness of the components, such that when the dressing is applied to a body portion, it conforms to the surface even when the surface is moved. When the surface is flexed and then returned to an un-flexed position, the facing layer stretches to accommodate the flexation of the joint but is resilient enough to continue to conform to the surface when the surface is returned to its unflexed condition.

A silicone facing layer has significant advantages over wound dressings that rely on a glue-type adhesive to secure a dressing to a wound. In particular, tacky silicone gels provide a coating which is exceptionally non-adherent to wounds, but which is significantly adherent to surrounding skin. Moreover, such gels are entirely immobile and unaffected by heat or body exudates. This means that dressings according to the invention retain their non-adherent properties even after they have been in place for a substantial period of time, for example, several days.

The silicone gel layer adheres gently to surrounding skin since it is inherently soft to the touch and flows partly into microscopic cavities and cracks in the skin to create a large contact area over the wound site. As a result, less adhesion force is required to secure the silicone layer over the wound site than in known dressings that include an adhesive layer having glue. Since the silicone layer more fully distributes its adhesion force, the peeling strength thereof does not strip epidermal cells when the dressing is removed from the wound site. Accordingly, the dressing can be reapplied without causing damage to the skin and wound at the wound site. Furthermore, the silicone layer prevents a moisture build-up under such a layer since it is hydrophobic and further since the capillary forces of the absorbent core draw the exudate into the dressing this enables the dressing to be lifted from the skin without causing pain to the wearer of the wound dressing.

The silicones which are used as the facing layer in the dressing of the invention preferably have a Shore A hardness less than 1, and most preferable have no measurable Shore A hardness.

When the silicones are formed by cross-linking a mixture of two or more silicones, the molecular weights of the various components and their degree of substitution by reactive groups may be different. This allows gels having different physical properties to be formed merely by varying the proportions of the components.

The composite facing layer also may include one or more skin treatment agents blended into the silicone elastomer, for example petroleum jelly and aloe vera. In a preferred example, up to 20% by weight of the composite elastic layer, preferably 11.9%, may be petroleum jelly, and up to 3%, preferably 0.1%, may be a secondary skin treatment agent such as aloe vera. It will be understood that different or additional skin treating agents may be utilized, depending upon the skin condition to be treated by the skin treating agent.

In a preferred embodiment, the silicone facing layer is formed as a silicone gel sheet having a predetermined pattern of apertures that are formed prior to the silicone gel sheet being bonded to the absorbent core. Typically, the apertures will have a diameter of 0.05 to 1.0 mm and there are approximately 50-350 apertures per cm^2. While in a preferred embodiment in FIG. 2 the apertures 34 are shown as generally being arranged in a uniform pattern, the facing layer 12 is not limited to this arrangement.

The silicone facing layer may be substantially planar along a proximal surface thereof. Moreover, the silicone facing layer may penetrate or fill surface irregularities of an absorbent core defined as openings, crevices or partial pores located along a surface thereof.

In another embodiment exemplified in FIG. 13, there may be a higher density of apertures 34 in the facing layer 12 corresponding to the central portion 22 of the dressing 10 while there is a lower density or absence of apertures 34 near or along the border portion of the dressing. Alternatively, the facing layer may entirely lack apertures at the border portion of the dressing, and more particularly, a region corresponding to the beveled portion of the absorbent core. This will mitigate fluid absorption at certain areas of the dressing, thereby more effectively directing the exudate absorption in areas that will more efficiently absorb exudate. Furthermore, in yet another embodiment, there is a greater concentration of apertures at or near portions of the absorbent core having the receptacles to thereby enhance exudate uptake towards such receptacles.

Notably, the facing layer is bonded only to the proximal surface of the absorbent core and may penetrate the absorbent core a distance approximately 50% of its thickness. By forming the apertures prior to bonding to the absorbent core, the facing layer does not occlude the cells nor coat the inside walls of the cells of the absorbent core. Accordingly, suitable permeability of the facing layer is preferably obtained by providing the facing layer with preformed apertures located in a suitable array, and accordingly, there is greater control in establishing the transit of fluid through the silicone gel layer.

The thickness of the facing layer may vary across the length thereof. For example, the facing layer may include regions having greater thickness near the border portion of the wound dressing as opposed to the central portion so as to provide greater strength to the facing layer at such regions thereof having a thicker facing layer.

In yet another embodiment, the facing layer may include at least two different layers having different properties. For example, a softer layer to be worn directly adjacent the wound site may be provided that closely conforms to the wound site while a harder layer may be provided that this interposed between the softer layer and the absorbent core to provide durability and strength to the dressing. The multiple layered or more aptly dual durometer facing layer adopts the principles described in U.S. Pat. No. 6,136,039 granted Oct. 24, 2000 owned by assignee of the invention described herein, the disclosure of which is incorporated herein.

In another embodiment, the facing layer of the present invention may comprise a silicone layer of the type mentioned above that is reinforced with an embedded perforated reinforcement layer. Such a reinforcement layer may include a non-woven, knitted or woven textile material, or a poymeric film such as one made of polyurethane. In this embodiment, the apertures in the silicone layer generally correspond to the perforations of the reinforcement layer.

It will be understood that non-silicone facing layers may be employed in the dressing of the present invention without departing from the scope thereof. Preferably, such facing layers should be soft, flexible, conformable, non-irritating and non-sensitizing. The dressing may include facing layers that comprise a perforated base film constructed of a variety of polymers such as polyurethane, polyethylene, polypropylene, polyamide or polyester material with a pressure-sensitive adhesive. Furthermore, the facing layer may be in the form of moisture vapor permeable films, perforated films, woven-, non-woven or knit webs or scrims. The adhesive may be a microsphere or fibrous adhesive with low trauma properties and have good adhesion to wet skin. It will be understood that the adhesive may be coated on only a portion of the facing layer, for example, the adhesive may be applied only around the border portion of the dressing with the central portion lacking an adhesive. Preferably, the facing layer should be perforated so as to permit transport of the fluid therethrough to the absorbent core.

The dressing the present invention can include various combinations of ingredients without departing from the scope of the present invention, including, for example, medicaments, soaps, disinfecting and sterilizing agents, odor management, hemostatic agents, proteins, enzymes and nucleic acids. Preferably these agents may be incorporated directly or dispersed in the absorbent core, or dispersed with the absorbent material. Alternatively, these ingredients may be incorporated into the dressing by any suitable means, including an additional layer to the absorbent core that would incorporate such ingredients.

Suitable medicaments, soaps, disinfecting and sterilizing agents, proteins, and enzymes are commercially available. Preferably such medicaments may include antifungal agents, antibacterial agents, angiogenesis promoting agents and other appropriate agents.

As mentioned above in observing FIG. 10, the facing layer 12 may include an adhesive that is provided near or at a peripheral border portion of the facing layer. Preferably, this adhesive is a pressure sensitive silicone such as an adhesive silicone manufactured by NuSil Technology (Carpenteria, Calif.) under product designation MED-1356 or a very tacky silicone manufactured by NuSil Technology (Carpenteria, Calif.) under product designation MED-6345. The adhesive silicone may applied to a silicone facing layer after the facing layer is cured such that the adhesive silicone is applied to the facing layer when it is in a partially cured state and then finishes curing when on the facing layer. Alternatively, the adhesive may be an acrylate glue or hot melt glue applied onto the facing layer using conventional methods for applying an adhesive to a substrate.

In a preferred method of the invention, the tacky silicone gel is prepared from a two-component silicone, such as MED-6340 parts A and B produced by NuSil Technology (Carpenteria, Calif.). The two parts A and B each include the same base, vinyl-substituted, poly(dimethylsiloxane). In addition, part A includes a platinum catalyst to facilitate a reaction between parts A and B when they are mixed. Part B includes a cross-link, hydride-containing silicone. Both parts A and B are easily mixed, and handled separately, do not react or cure.

The tacky silicone gel is produced by thoroughly mixing parts A and B in a ratio of 1:1, thereby enabling the vinyl-group on the vinyl-substituted silicone to be activated by the catalyst and the hydride containing silicone. This results in cross-linking the silicone so that it will begin to cure. One of the factors that influences the time required for curing is the temperature of the mixed combination of parts A and B. A suitable temperature range is 50-150° C., preferably 100-130° C. Another factor that influences the curing time is the amount of catalyst that is used in the combination of parts A and B, however the catalyst may also undesirably influence the tackiness of the silicone gel. Typically, in the present invention, the curing time of a 0.1 mm thick silicone gel facing layer cured at 100° C. is approximately 1 minute, and the silicone gel facing layer is normally transferred to the absorbent core when it is in a partially cured state in a range of 3-12 seconds after parts A and B have been mixed.

It will be understood that the aforementioned steps for preparing the tacky silicone gel are provided for exemplary purposes and the invention is not meant to be limited by such steps. Any suitable steps for preparing a partially cured tacky facing layer may be used while still being within the scope of the present invention.

In the context of the present invention, "partially cured" silicone denotes that the silicone is not completely cured and therefore the silicone is not fully cross-linked. Typically, the parameters for yielding a partially cured silicone layer must be established empirically with respect to the gel mixture and absorbent material used. While the parameters for yielding a "partially cured" silicone layer may vary, the ratio of time required for the silicone gel to become fully cured may be employed to determine if the silicone layer is partially cured. Specifically, in the present invention, the silicone layer is partially cured between 5-70% of the total time required to cure the silicone gel. It follows that the time interval to apply the facing layer to the absorbent core is between 5-40%, or more preferably 5-20%.

When curing the silicone layer, a catalyzer may be used to speed up the curing time and reduce the tackiness of the silicone gel. A silicone catalyzer is commercially available from NuSil Technology (Carpenteria, Calif.) under the product designation CAT-50.

Figure 14:
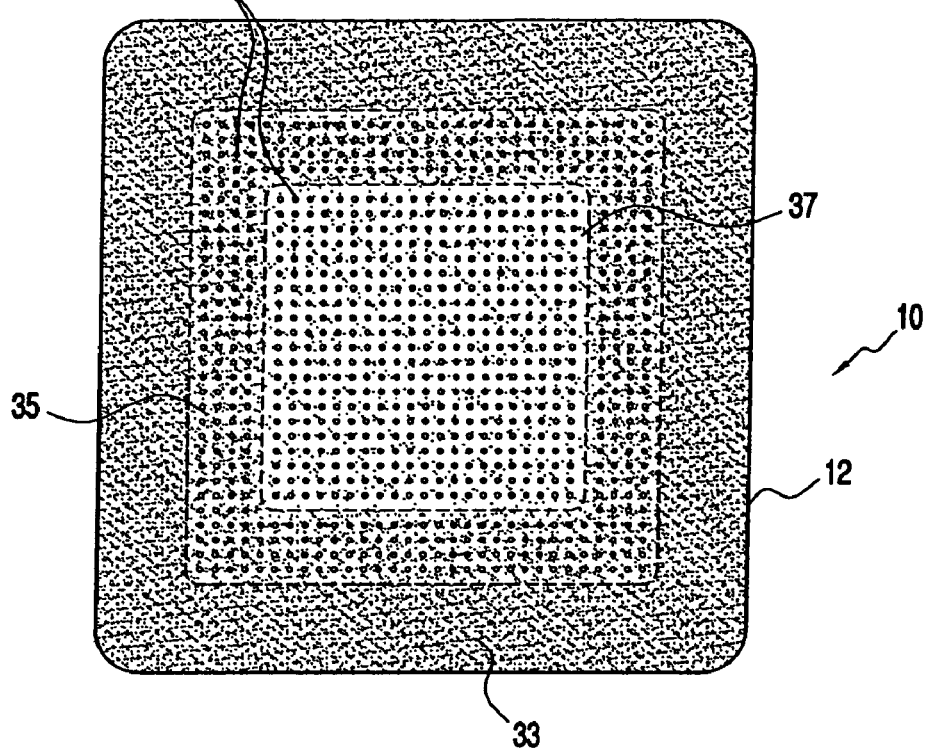

Another preferable feature of the facing layer of the present invention is a variable tackiness across the surface thereof. According to this feature, the tackiness of the facing layer is configured differently at different regions thereof. For example, regions of the facing layer near or at the border portion of may be provided with a greater tackiness than the central portion of the facing layer. The tackiness may be disposed in a gradient across a half section of the facing layer from a maximum at or near the border portion of the facing layer to a minimum at or near the central portion of the facing layer. An embodiment of the wound dressing having a facing layer 12 with variable tackiness is exemplified in FIG. 14. As shown, the facing layer 12 may be provided in discrete multiple sections having generally uniform tackiness such as a border portion 33 having greater tackiness than a central portion 37 and an intermediate portion 35 of the facing layer 12. The tackiness may gradually increase from the central portion 37 towards the border portion 33, or the tackiness may remain relatively constant in each discrete portion 33, 35, 37.

Figure 15:
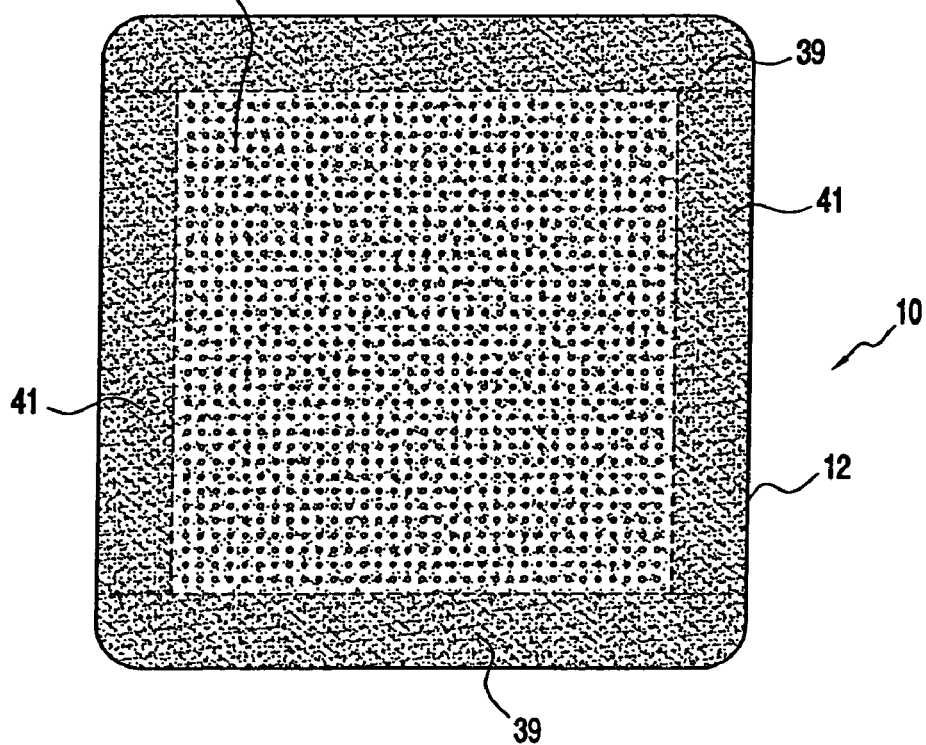

The facing layer is not limited to a border portion having a uniform tackiness. The facing layer may include at least one side of the border portion having tackiness greater than other portions thereof. For example, as exemplified in FIG. 15, if the dressing has a generally square or rectangular configuration, two opposing sides 39 corresponding to the border portion of the facing layer 12 may have a greater tackiness than the remaining opposing sides 41 of the facing layer. Alternatively, in the event the dressing has a generally circular configuration or variations thereof, as shown in FIG. 16, sections 43 of the facing layer 12 corresponding to the border portion thereof may have a greater tackiness than other sections of the border portion of the facing layer 12.

According to a 90° peel-off test from a stainless steel surface, the tackiness corresponding to the central portion of the silicone facing layer is generally within the range of 0.05 N - 1.0 N and preferably within the range of 0.1 N to 0.4 N. The tackiness corresponding to the border portion of the silicone facing layer is within the range of 0.5 N - 5.0 N and preferably within the range of 0.8 N - 3.0 N.

The facing layer with variable tackiness may be obtained by forming a facing layer wherein areas thereof have different mixtures of silicone components, the presence or different quantities of silicone catalyzer or other components, exposure to different curing conditions such as pressure or temperature, or any other method known to one skilled in the art of obtaining different tackiness in a silicone substrate. Moreover, in the embodiments such as those exemplified in FIGS. 14-16, discontinuous discrete sections of the facing layer having different tackiness can be prepared and applied to the absorbent core separately or the facing layer can be formed with a continuous facing layer having discrete sections of different tackiness.

In another embodiment of the wound dressing exemplified in FIG. 17, the backing layer 16 may be configured so as to define a border section 45 that extends beyond the border of the absorbent core 14 and the facing layer 12 disposed thereon. The border section 45 of the backing layer 16 preferably surrounds the peripheral edges of the absorbent core 14 and the facing layer 12. The border section 45 of the backing layer 16 may be provided with a skin adherent adhesive or an elastomeric gel that is preferably tackier than the facing layer 12. The stronger adhesion of the border section 45 of the backing layer 16 permits the dressing 10 to remain firmly in place over a wound site. In this embodiment, the facing layer 12 preferably has a gentle adhesion that will prevent traumatization of a wound upon removal therefrom.

In yet another embodiment shown in FIG. 18, the backing layer 16 is adhered to the absorbent core 14 such that the absorbent core extends from the backing layer 16. The facing layer 12 is configured to extend around the sides of the absorbent core 14 and will generally extend to meet with the backing layer 16. The backing layer 16 includes a border section 45 that may have a stronger tackiness than the facing layer 12.

In the embodiments shown in FIGS. 17 and 18, the backing layer may be provided with or without the aforementioned compliant element and the absorbent core may be provided with or without the receptacles containing discrete portions of absorbent material.

The entirety of the side of the backing layer adjacent the absorbent core may include the skin adherent adhesive or an elastomeric gel used for the border section 45. In a such an embodiment, the skin adherent adhesive or an elastomeric gel, however, is preferably disposed on the backing layer so that it does not prevent moisture transfer therethrough. In the alternative, the skin adherent adhesive or an elastomeric gel disposed on the border section of the backing layer may be applied, such as sprayed or spreaded, to the border section of the backing layer after the backing layer is applied to the absorbent core.

The method of manufacturing this embodiment may be conducted using one of the methods described herein for applying the backing layer to the absorbent core. Alternatively, one side of the backing layer may be coated with a discontinuous adhesive or elastomeric gel on a side that will face the absorbent core. The backing layer is thus placed onto the absorbent core so that the backing layer extends over an entire surface thereof wherein a section of the backing layer extends beyond the peripheral edges of the absorbent core to define the border section. Prior to applying the backing layer to the absorbent core, a primer may be applied to the side of the absorbent core adjacent to the backing layer such that the primer is applied discontinuously so that the primer does not prevent transport of moisture through the backing layer when applied on the absorbent core.

In a preferred method, the facing layer and its apertures are formed prior to being bonded onto the absorbent core. A perforation device 42 is preferably used to form the facing layer and its apertures. As shown in FIGS. 19 and 20, the perforation device 42 includes a generally planar carrier surface 47 having a plurality of needle-like perforating elements 44 that extend a distance therefrom. The perforation device 42, including the carrier surface 47 and the perforating elements 44, is selectively heated to a curing temperature of the silicone. The carrier surface 47 and the perforating elements 44 are coated with a release film, such as TEFLON.

In a preferred embodiment, the perforating elements extend a distance slightly greater than the thickness of the silicone layer, and can vary in length from 0.02 to 1.0 mm with a preferable length of 0.1-0.2 mm. While in this embodiment the perforating elements have a generally circular cross-section, the pins are not limited to this configuration. For instance, the pins may alternatively have a cross-section configured in a triangular, square, rectangular or any other suitable shape or combination thereof. The perforation device has a density of 5 to 300 perforating elements per cm^2, and preferably there are 100 perforating elements per cm^2.

When forming the facing layer, a discrete layer of uncured silicone gel is disposed on the carrier surface of the perforation device such that the perforation elements extend through the layer of silicone gel. The uncured silicone layer generally has a thickness ranging between 0.05-0.5 mm. The perforation device is heated to a predetermined temperature, about 100° C. or to any other suitable curing temperature of the silicone gel, either before or after the silicone gel is placed thereon. The silicone gel will begin to cure along an inner side portion thereof that is adjacent to the carrier surface as it is smoothed over the carrier surface. It will be understood, however, that it is not desirable that an outer side portion of the silicone gel that is opposed to the inner side portion of the silicone gel fully cure. This is so that the outer side portion will have sufficient tackiness to adhere to the absorbent core when pressed thereagainst and will thus enable the silicone gel to finish curing while disposed on the absorbent core itself.

The absorbent core is placed on the side of the facing layer that is opposite the side adjacent the carrier surface. Since the silicone gel is in a partially cured state, the silicone gel will cure and adhere to the surface of the absorbent core. When the silicone gel has fully cured, the silicone layer is removed from the perforation device along with the absorbent core. Pressure may be exerted onto the absorbent core and the facing layer to more fully adhere the facing layer to the absorbent core.

The silicone layer may be removed from the perforation device prior to be being applied to an absorbent core. In this instance, the silicone layer may be peeled away from the perforation device when it is in a partially cured state, thus forming a discrete, partially cured silicone layer that can be applied to a transfer film or substrate for future application to an absorbent core or directly to a body member. The transfer film may be an air permeable paper or similar type of film or paper that will easily permit the silicone layer to be applied and removed therefrom when substantially or fully cured.

The perforation device may be modified in view of the description provided above. Specifically, the carrier surface of the perforation device may include a plurality of holes extending therethrough wherein a plurality of discrete perforation elements is slidably disposed through the plurality of holes. The method for using this perforation device includes the steps of heating the planar surface and perforating elements of the perforation device, and placing a layer of uncured silicone gel on the planar surface of the perforation device. Once disposed upon the planar surface, the perforation elements are driven through the silicone layer. After the silicone layer is at least partially cured, the perforation elements are withdrawn from the silicone gel layer. An absorbent core may then be applied onto the silicone layer as the silicone layer cures. Alternatively, the silicone layer may be left to fully cure on the perforation device and then subsequently removed, or the silicone layer may be removed prior to fully curing.

Figure 21:
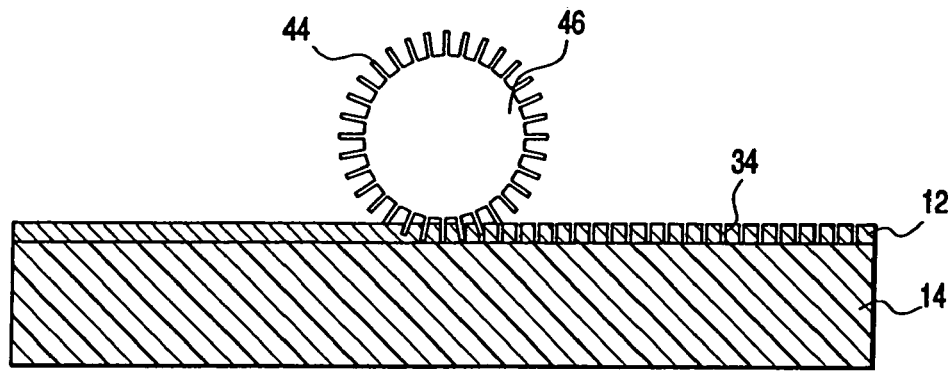
FIGS. 21-23 are schematic views showing arrangements for forming apertures in facing layers of the invention.

In another method for applying the facing layer to the absorbent core in the present invention, a partially cured, silicone layer 12 is deposited onto a transfer film upon which apertures are formed in the silicone layer 12 by rotating a mechanical roller 46 thereon. As exemplified in FIG. 21, the mechanical roller 46 has a patterned surface that is similar in construction to the carrier surface 47 and the perforation elements 44 of the aforesaid perforation device 42 depicted in FIGS. 19-20. In forming the apertures, perforation elements 44 of the mechanical roller 46 are heated to about 100° C. or to the curing temperature of the silicone layer. The mechanical roller 46 may either be applied against the partially cured silicone layer after the silicone layer 12 has been applied to the absorbent core 14 or may be applied against the silicone layer while adhered to a transfer film prior to the application thereof to the absorbent core.

The mechanical roller may include the slidable perforating elements, as described in reference to an embodiment of the perforating device and function generally in the same way.

In another method, uncured silicone gel may be extruded directly onto a heated mechanical roller, similar to the type described above, rotating at a predetermined speed. A length of the absorbent core material is supported by a conveying surface and positioned below the mechanical roller. As the mechanical roller rotates, the partially cured silicone gel is deposited onto the absorbent core material by the rotating mechanical roller which applies at least a slight pressure on the absorbent core. The mechanical roller is configured and arranged to rotate at a sufficient speed so that the silicone gel will be nearly or fully cured as it leaves the carrier surface and is applied to the absorbent core.

A silicone primer, such as a silicone primer manufactured by NuSil Technology (Carpenteria, Calif.) under product designation CF6-135, may be used to facilitate the bonding of the silicone layer to the absorbent core.

Figure 22:
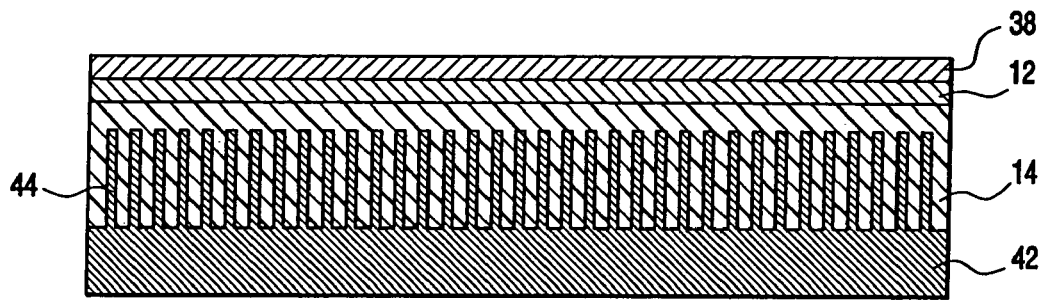

In yet another method for applying a facing layer to an absorbent core, as exemplified in FIG. 22, a partially cured, non-perforated silicone layer 12 may be applied to a transfer film 38. The film 38 carrying the silicone layer 12 is then reversed in orientation so that the film 38 defines an upper surface and the silicone layer 12 defines a lower surface. The silicone layer 12 is then slowly positioned on an upper surface of the absorbent core 14. After the silicone layer 12 is gently pressed onto the absorbent core 14, a perforation device 42 carrying a plurality of perforating elements 44 having a similar construction to the aforementioned perforation device 42 depicted in FIGS. 19 and 20 is positioned over a lower surface of the absorbent core 14. This perforation device 42, however, is distinct from the perforation device of FIGS. 19 and 20 in that each of the perforating elements 44 includes a discrete air passageway and may generally be larger therefrom.

The perforating elements 44 are inserted into at least a portion of the thickness of the absorbent core 14 and air is blown through the projection elements 44 towards respective portions of the silicone layer 12. The air blown through the perforating elements 44 cures the silicone layer 12 and further forms apertures through the silicone layer 12. After an adequate period of time and upon formation of the apertures, the device 42 carrying the needles 44 is withdrawn from the absorbent core 14. The film 38 is subsequently removed from the silicone layer 12. A silicone primer, as described above, may be applied to the absorbent core 14 to the application of the silicone layer 12 thereon to improve the adherence of the silicone layer to the absorbent core.

Figure 23:
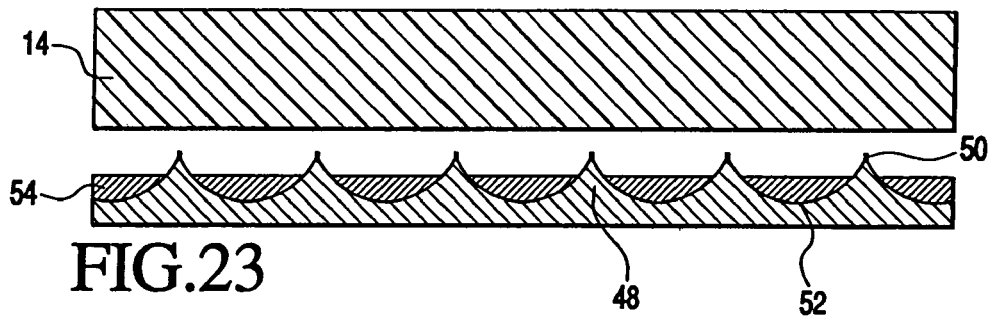
Figure 24:
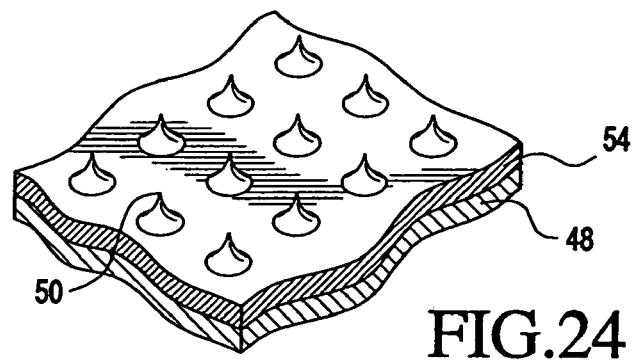
FIG. 24 is a perspective view of an arrangement for forming apertures in the facing layer of the wound dressing of FIG. 23.
Figure 25:
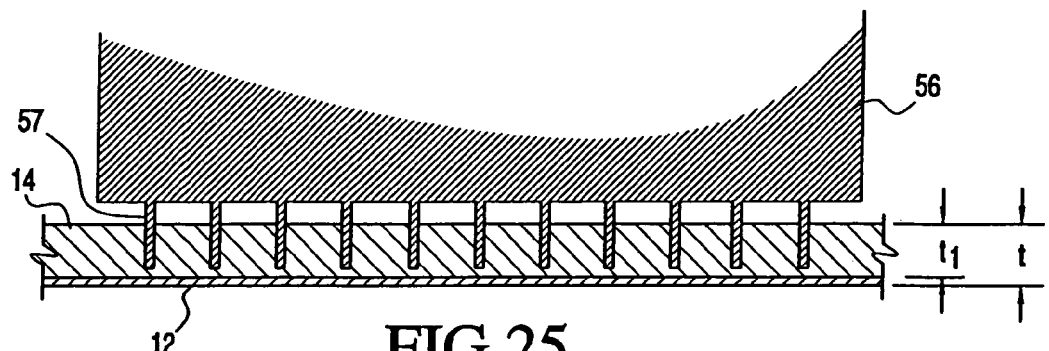
FIGS. 25-26 are schematic views showing an arrangement for forming receptacles in an absorbent core of the invention.
Figure 26:
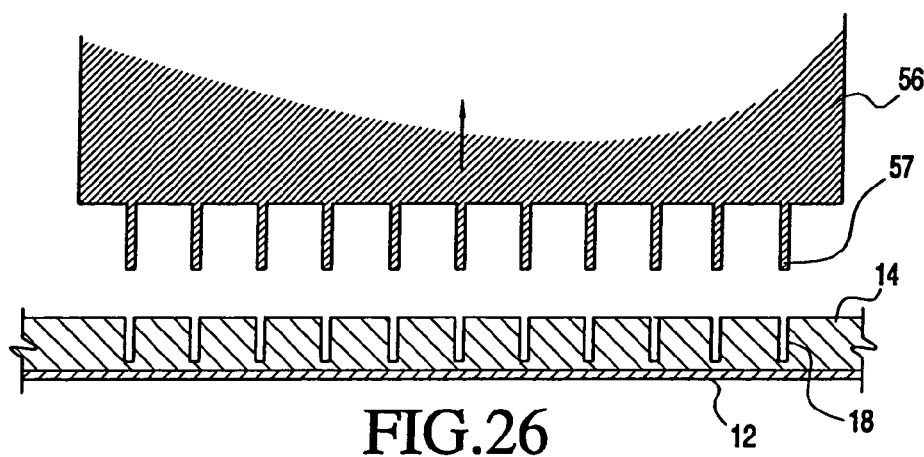
Figure 27:
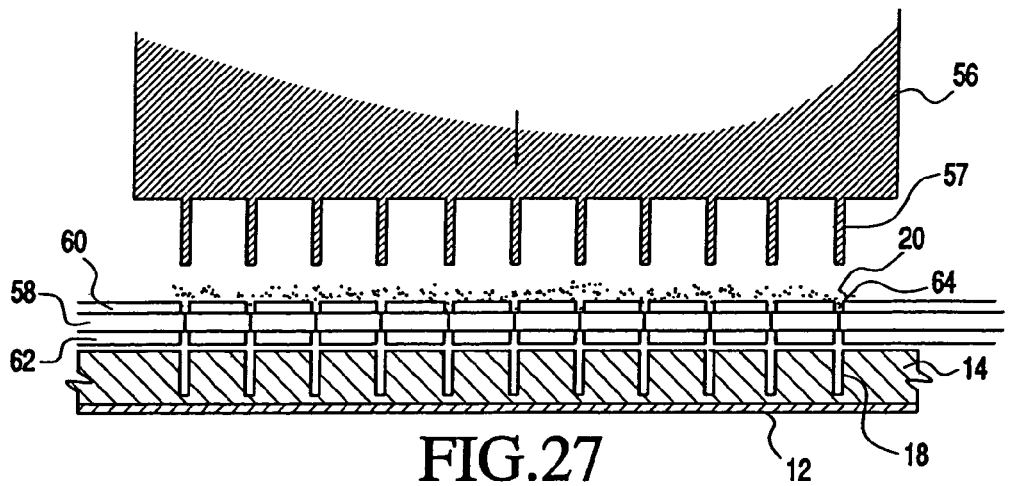
FIGS. 27-28 are schematic views showing an arrangement for depositing discrete portions of absorbent material in receptacles of an absorbent core of the invention.
Figure 28:
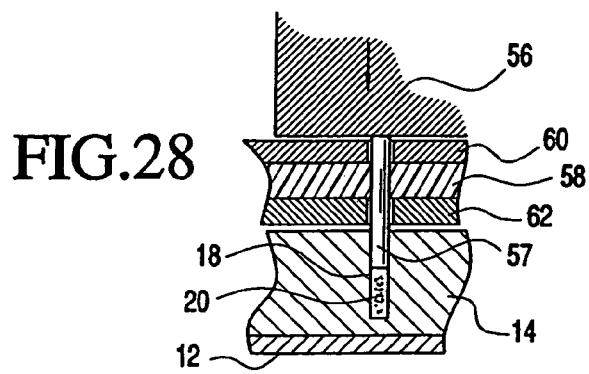

In yet another method exemplified in FIGS. 23 and 24 for applying the facing layer 12 to the absorbent core 14, a patterned negative surface 48 is provided that bears the negative impression of the eventual silicone layer 12. The patterned surface 48 includes a series of peaks and valleys 50, 52 that correspond to the eventual pattern of apertures of the silicone layer 12. A partially-cured silicone gel 54 is applied to the patterned surface 48 whereupon the silicone gel 54 rests in the valleys 52 while at least a top portion of the peaks 50 extend therethrough. The absorbent core 14 is subsequently positioned over the silicone gel 54 with the top portion of the peaks 50 penetrating the absorbent core 14. The silicone gel 54 is then bonded to the absorbent core 14 and the patterned surface 48 is removed from the thus formed silicone layer 12. Removal of the patterned surface 48 imparts a predetermined pattern of apertures on the silicone layer 12 that correspond to the peaks 50 of the patterned surface 48.

In yet another method for applying a facing layer to an absorbent core, a silicone gel is mostly cured in a container. At a moment in which the silicone gel has reached a suitably thick consistency, the silicone is sprayed onto the absorbent core in a systematic manner so as to adhere thereto. While the silicone is sprayed onto the absorbent core, a plurality of apertures is formed along the silicone layer. The spraying of the silicone is conducted in a controlled manner that permits the holes to be formed in a non-random, predetermined pattern. The silicone layer may be sprayed onto the absorbent core so as to include an undulating surface.

In each of the aforesaid methods for applying a facing layer onto an absorbent core, it is essential that the silicone does not coat the walls of the cells or pores of the absorbent core. The objective is not to occlude the cells or pores with silicone and provide uninhibited transport from the facing layer to the absorbent core. Furthermore, it is preferred that the holes formed through the silicone facing layer of the invention be arranged in a predetermined pattern so as to provide greater control of the fluid that passes through the silicone facing layer when the dressing of the invention is applied to a wound site.

In any of the foregoing methods, the facing layer and the absorbent core are adhered to each other substantially uniformly along their opposed areas. Furthermore, in each of the foregoing methods, the apertures of the facing layer may be formed either before or after the facing layer is applied to the absorbent core. The perforating elements or peaks may or may not extend a distance into the absorbent core if the absorbent core is applied to the facing layer while the facing layer is positioned on a perforation device. It will be understood, that it is preferred that the facing layer be partially cured when applied to the absorbent core so as to be sufficiently tacky to adhere to the absorbent core, yet substantially cured so that additional apertures are not formed therethrough by capillary action of the cells or pores of the absorbent core.

In a method exemplified in FIGS. 25-28, the preparation of the absorbent core 14 of the dressing 20 of the invention may be conducted as follows. First, a plurality of projection elements 57 are heated to a suitable temperature and are inserted into a surface of the absorbent core 14. The projection elements 57 are heated to a temperature in the range of 200-300° C., preferably 255° C. The projection elements 57 extend into the absorbent core 14 a distance less than its total thickness. The projection elements 57 are preferably arranged in a pattern bearing the negative impression of the receptacles 18 of the absorbent core 14. The projection elements 57 are removed from the absorbent core 14 after a period of time, thereby forming the receptacles 18 in the absorbent core 14.

The discrete portions of absorbent material 20 are deposited into the receptacles 18 by positioning a silicone film 58 between aligned top and bottom plates 60, 62 having a plurality of holes 64 corresponding to the plurality of projection elements 57 used to form the receptacles 18. A predetermined amount of the absorbent material 20 is deposited into each of the holes of the top plate 60 and the projection elements 57 used to form the receptacles are inserted through the plurality of holes of the top and bottom plates 60, 62, and the silicone film 58 so as to deposit and compact the absorbent material 20 into each of the receptacles 18.

While the bulk amount of absorbent material in each receptacle may be varied, it is preferred that the amount of absorbent material should not fill the entire receptacle since wetted absorbent material will swell. It will also be understood that it is important to the method that the portions of the absorbent material not be compacted in the receptacles to the degree that migration of such absorbent material is obstructed.

It will be understood that the present invention is not limited to the aforementioned method for depositing the absorbent material in the receptacles. Any method that may permit insertion and compaction of discrete portions of absorbent material in the receptacles in a controlled fashion may be employed while still remaining within the scope of the invention.

For example, a simple approach for depositing absorbent material in the receptacles, in the event that superabsorbent granulates or powders are used, comprises the step of depositing the absorbent material into each of the receptacles and then brushing, blowing or wiping off excess absorbent material from the surface of the absorbent core. A vibration table or similar vibration mechanism may be used to urge the absorbent material to settle in the receptacles.

In the aforementioned method, it will be understood that the facing layer and the absorbent core are at least adhered and sealed to each other at the border portions thereof. The importance of this is that the facing layer must be secured to the absorbent core so that the discrete portions of absorbent material do not leak from the wound dressing.

A method for securing the backing layer 16 to the absorbent core 14 and formation of the compliant element 26 is preferably performed as illustrated in FIGS. 29-34. In a preferred method, a platen 66, as shown in FIG. 29, may be provided and configured with a profiled surface 70 corresponding to the compliant element 26 and the central 22, intermediate 23 and border portions 24 of a dressing of an embodiment of a wound dressing of the invention. The platen 66 is selectively in communication with a vacuum configured to draw a vacuum along its profiled surface 70 and is heated to a temperature in the range of 150-200° C., preferably 185° C. In a preferred embodiment, the platen 66 includes a groove 68 that extends around the profiled surface 70 that defines the form of the compliant element 26. The platen 66 includes at least one passageway 72 in communication with the groove 68 and a vacuum. The platen 66 may also include a knife edge 74 that extends around the peripheral edge of the profiled surface 72 and a beveled portion 76 near the peripheral edge.

The platen 66 includes at least one recessed portion, such as recessed portions 78, 80, 82 and 84 shown in FIG. 29, that may be disposed about a central portion of the platen 66. The recessed portions 78, 80, 82 and 84 are preferably defined in a step-wise configuration with the central recessed portion 84 being relatively deeper than a first recessed portion 78. The at least one recessed portion is provided to reduce the pressure exerted at the localized region of the corresponding absorbent core. This results, at least in part, in decreasing the level of adherence of the backing layer at such localized region to the absorbent core. It will be noted that the platen is not limited having recessed portions only in a central portion thereof and may be provided along any portion of the platen where it is desired to have a localized region of less adherence of a backing layer to an absorbent core.

The platen 66 may include a plurality of such passageways 72 that are utilized to communicate the vacuum with a backing layer 16. For example, the platen 66 may include 8 equally spaced passageways about the groove 68 when an absorbent core has a generally rectangular shape. In this example, a passageway may be provided at a location corresponding to intermediate portion of the absorbent core and a passageway may be provided between each corner. Moreover, the platen may include at least one additional passageway 73 that is in communication with compressed air, and such at least one additional passageway may be disposed on the platen corresponding to either the central or border portions.

It will be noted that the platen may be configured according to the shape of the eventual wound dressing and its individual features. For example, the platen may be arranged in a generally circular shape having a groove that is generally circular.

As shown in FIG. 30, the backing layer 16 is placed over the absorbent core 14, and then, as shown in FIG. 31, the platen 66 is positioned against the backing layer 16 and draws the backing layer 16 towards its profiled surface 70 by the vacuum. The platen 66 is continually drawn towards the absorbent core 14 while drawing the backing layer 16 against its profiled surface 70. Of note is that a portion of the backing layer 16 is preferably drawn into the groove 68, thereby forming at least a portion of the compliant element 26. In FIG. 31, the platen 66 is heated at portions of the profiled surface 70 corresponding to the central, intermediate and border portions 22, 23, 24 of the eventual dressing. The surface of the groove 68 may or may not be heated.

Figure 32:
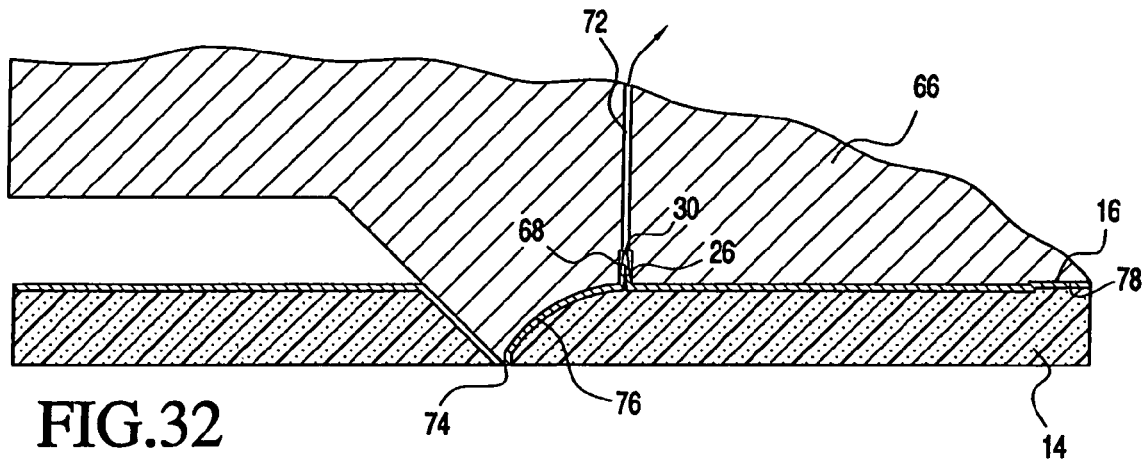
Figure 33:
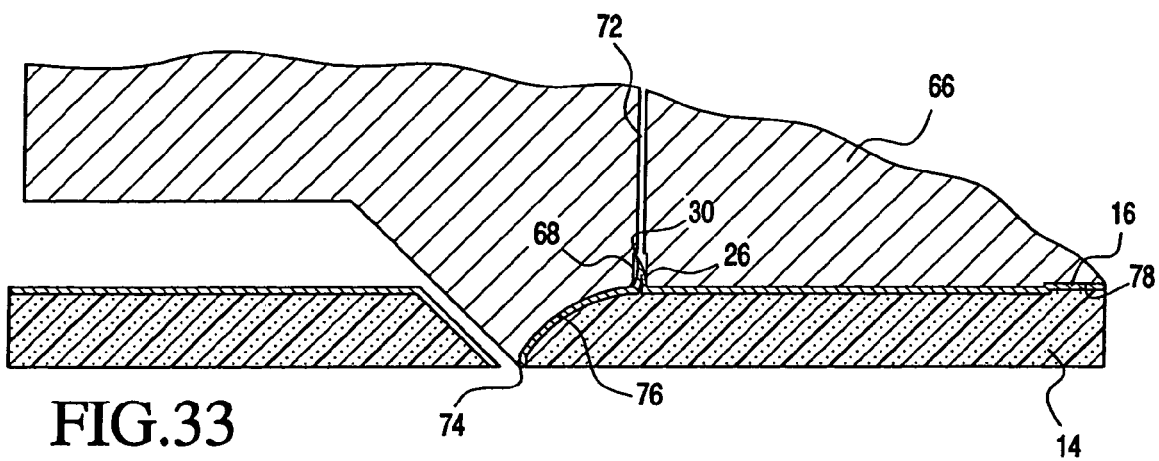
Figure 34:
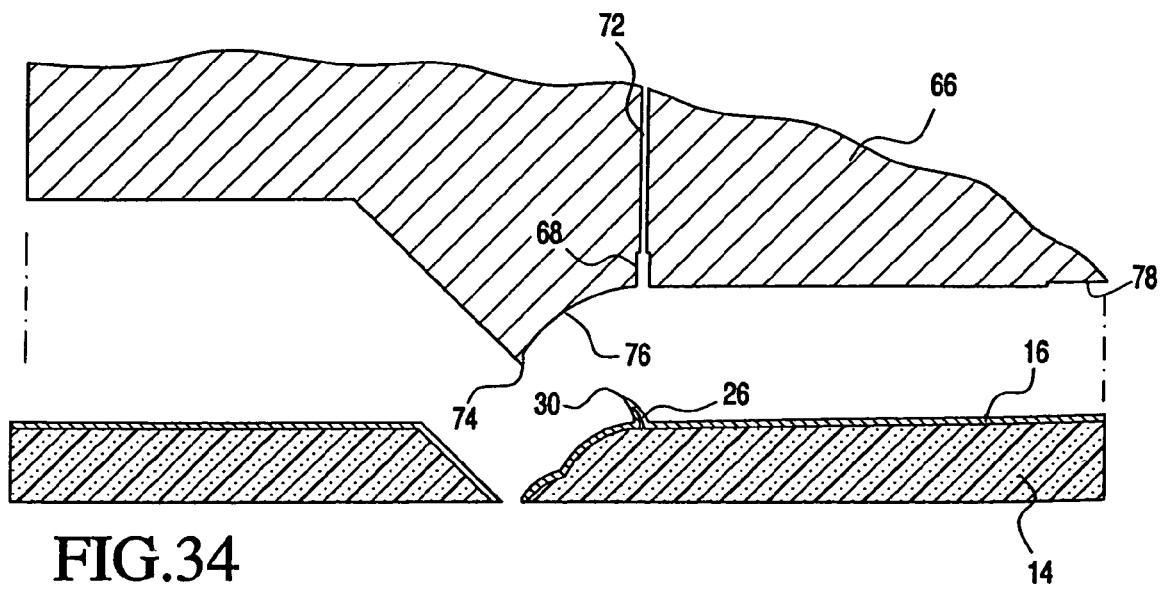

In FIG. 32, the platen 66 positions the backing layer 16 against the absorbent core 14. As can be seen in FIG. 33, the knife portion 74 effectively cuts the absorbent core 14 and backing layer 16, and imparts the beveled portion 28 of the border portion 24 to the dressing 10. Prior to withdrawing the platen 66 from the absorbent core 14, as shown in FIG. 33, the vacuum is removed from the profiled surface 72 and air projected against the backing layer generally at the central portion thereof. As illustrated in FIG. 34, the platen 66 is subsequently removed from the formed absorbent core 14 with the backing layer 16.

In another embodiment, the profiled surface of the platen may be configured so that a central portion thereof corresponding to the central portion of the dressing extends so that it imparts a thickness to the absorbent core that is less than at the area corresponding to the compliant layer and the border portion. This is so that the backing layer will adhere more loosely to the absorbent core at the central portion of the wound dressing. Due to the difference in thickness of the absorbent core, the dressing will have the benefit that the discrete portions of absorbent material will cause the backing layer to detach from the absorbent core more effectively, and will further prevent the backing layer from detaching from the border portion of the dressing before detaching at the central portion of the dressing.

It will be understood that the above described embodiments of the invention may assume a variety of different shapes, sizes and configurations without departing from the scope of the present invention.

It will be understood that the above described embodiments of the invention are illustrative in nature, and that modifications thereof may occur to those skilled in the art. Accordingly, this invention is not to be regarded as limited to the embodiments disclosed herein, but is to be limited only as defined in the appended claims.

We claim:

1. A wound dressing for covering a wound, comprising:
a discrete skin adherent and resilient facing layer formed from a compound consisting of a hydrophobic silicone gel and a skin treatment agent selected from the group consisting of aloe vera and petroleum jelly, the facing layer having a plurality of preformed and uniformly shaped apertures arranged in a pattern;
wherein the shape of the facing layer is defined by opposed, generally continuously planar outermost first and second surfaces, the apertures solely formed between the outermost first and second surfaces; and
wherein one of the outermost first and second surfaces of the facing layer is in a partially cured state.

2. The wound dressing according to claim 1, wherein the plurality of apertures arranged in the pattern vary in number per unit area according to their location relative to a center axis of the silicone gel layer.

3. The wound dressing according to claim 1, wherein the plurality of apertures arranged in the pattern vary in size according to their location relative to a center axis of the silicone gel layer.

4. The wound dressing according to claim 1, wherein the apertures are generally circular.

5. The wound dressing according to claim 1, wherein the apertures are generally equally spaced from one another.

6. The wound dressing according to claim 1, wherein the pattern of the apertures comprises alternating apertures of at least two different sizes.

7. The wound dressing according to claim 6, wherein the apertures have two different sizes, the first size being larger than the second size and the apertures of the first size being bordered by the apertures of the second size.

8. The wound dressing according to claim 7, wherein the apertures of the second size are bordered by the apertures of the first size.

9. The wound dressing according to claim 1, wherein the silicone gel layer has a progressive increase of tackiness extending from a central portion to a border portion thereof.

10. The wound dressing according to claim 1, wherein the silicone gel layer has regions of varying thickness.

11. The wound dressing according to claim 1, wherein the apertures of the facing layer have a diameter within the range of 0.05 to 1.0 mm, and have a density of 50 to 350 apertures/$cm^2$.

12. A wound dressing for covering a wound, comprising:
a discrete skin adherent and resilient facing layer formed from a compound consisting of a hydrophobic silicone gel, the facing layer having a plurality of preformed apertures arranged in a and non-apertured regions of the facing layer consisting of the silicone gel;
wherein the shape of the facing layer is defined by opposed, generally continuously planar outermost first and second surfaces, the apertures solely formed between the outermost surfaces; and
wherein one of the outermost first and second surfaces is in a partially cured state.

* * * * *